US008933050B2

(12) United States Patent
Friedlander et al.

(10) Patent No.: US 8,933,050 B2
(45) Date of Patent: Jan. 13, 2015

(54) METHODS FOR THE TREATMENT AND THE DIAGNOSIS OF CANCER

(75) Inventors: Gérard Friedlander, Paris (FR); Laurent Beck, Nantes (FR); Christine Salaün, Glasgow (GB); Christine Leroy, Paris (FR)

(73) Assignees: Institute National de la Sante et de la Recherche Medicale (INSERM), Paris (FR); Universite Paris Descartes, Paris (FR); Assistance Publique—Hopitaux de Paris, Paris (FR)

( * ) Notice: Subject to any disclaimer, the term of this patent is extended or adjusted under 35 U.S.C. 154(b) by 0 days.

(21) Appl. No.: 13/819,911

(22) PCT Filed: Sep. 2, 2010

(86) PCT No.: PCT/IB2010/002452
§ 371 (c)(1),
(2), (4) Date: Mar. 1, 2013

(87) PCT Pub. No.: WO2012/028899
PCT Pub. Date: Mar. 8, 2012

(65) Prior Publication Data
US 2013/0156702 A1 Jun. 20, 2013

(51) Int. Cl.
*C12N 15/11* (2006.01)
*A61K 39/395* (2006.01)
*A61K 49/00* (2006.01)
*C12Q 1/68* (2006.01)
*A61K 31/7052* (2006.01)
*A61K 38/02* (2006.01)

(52) U.S. Cl.
CPC .......... *A61K 49/0008* (2013.01); *C12Q 1/6886* (2013.01); *A61K 31/7052* (2013.01); *A61K 38/02* (2013.01); *A61K 39/39558* (2013.01); *A61K 49/00* (2013.01); *C12Q 2600/112* (2013.01); *C12Q 2600/158* (2013.01)
USPC ..................................... 514/44 A; 424/130.1

(58) Field of Classification Search
CPC .. C12Q 1/6886; C12Q 1/6883; C12Q 1/6809; C12Q 2600/178; A61K 2300/00; C12N 15/86
See application file for complete search history.

(56) References Cited

U.S. PATENT DOCUMENTS

2005/0260639 A1* 11/2005 Nakamura et al. ................ 435/6
2009/0162361 A1* 6/2009 Nakamura et al. ......... 424/138.1

FOREIGN PATENT DOCUMENTS

WO  2004/031413 A2  4/2004

OTHER PUBLICATIONS

Sun (Cancer Biology & Therapy 2007 vol. 6 No. 10 pp. 1532-1538).*
Li et al, Role of the Sodium-Dependent Phosphate Cotransporter, Pit-1, in Vascular Smooth Muscle Cell Calcification, 2006, Circulation Research, 98: 905-912.*
Anonymous, "GeneChip Human Genome U95 Set Human Genome U133 Set GeneChip Human Genome U133 Plus 2.0 Array", Affymetrix, Jan. 1, 2009, Web.
Sundberg et al., "Microchip-based systems for target validation and HTS", Drug Discovery Today, Jan. 1, 2000, pp. S92-S103, vol. 5, Elsevier, New Jersey.
Kasamatsu et al., "Identification of candidate genes associated with salivary adenoid cystic carcinomas using combined comparative genomic hybridization and oligonucleotide microarray analyses", International Journal of Biochemistry and Cell Biology, Sep. 1, 2005, pp. 1869-1880, vol. 37, No. 9, Exeter, GB.
Beck et al., "Identification of a Novel Function of PiT1 Critical for Cell Proliferation and Independent of Its Phosphate Transport Activity", Journal of Biological Cheistry, Nov. 6, 2009, pp. 31363-31374, vol. 284, No. 45, American Society for Biochemistry and Molecular Biology, Inc, US.
Beck et al., "The Phosphate Transporter PiT1 (Slc20a1) Revealed as a New Essential Gene for Mouse Liver Development", PLOS ONE, Sep. 6, 2009, pp. E9148/1-E9148/14, vol. 5, No. 2.
Fernandes et al., "NaPO4 cotransport type III (PiT1) expression in human embryonic kidney cells and regulation by PTH", American Journal of Physiology: Renal Fluid and Electrolytephysiology, Oct. 1, 1999, pp. F543-F551, vol. 277, No. 4, American Physiology Society, US.

* cited by examiner

*Primary Examiner* — Tracy Vivlemore
*Assistant Examiner* — Kate Poliakova
(74) *Attorney, Agent, or Firm* — Whitham, Curtis, Christofferson & Cook, P.C.

(57) ABSTRACT

The present invention relates to methods for the diagnostic and the staging of cancer such as liver cancer. The present invention also relates to methods for the treatment of cancer including liver cancer such as hepatocellular carcinoma (HCC).

5 Claims, 5 Drawing Sheets

METHODS FOR THE TREATMENT AND THE DIAGNOSIS OF CANCER

FIELD OF THE INVENTION

Figure 1:
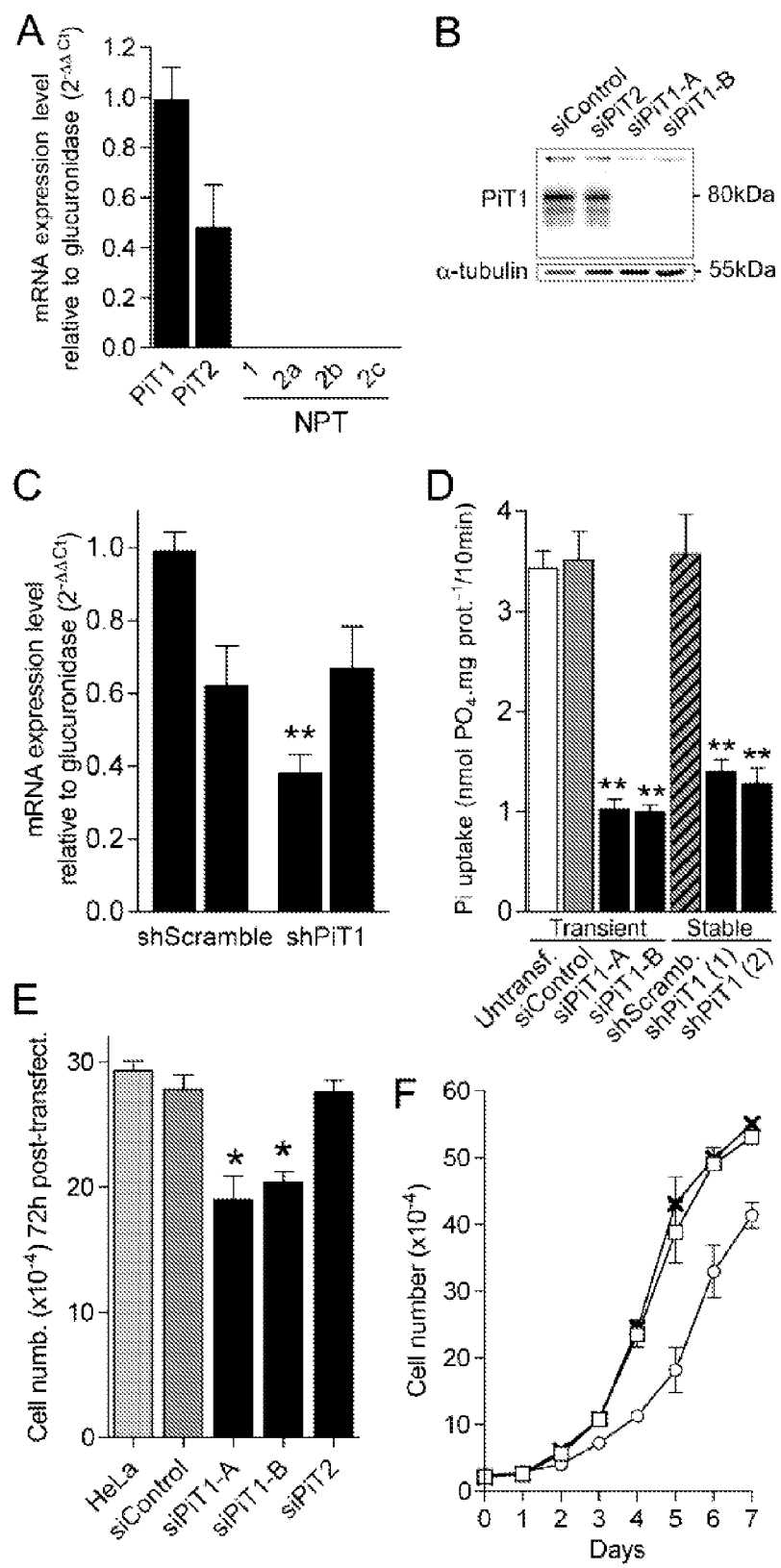

The present invention relates to methods for the diagnosis and the staging of cancer such as liver cancer. The present invention also relates to methods for the treatment of cancer including liver cancer such as hepatocellular carcinoma (HCC).

BACKGROUND OF THE INVENTION

PiT1 belongs to the inorganic phosphate (Pi) transporter (PiT)[3] family (Transport Classification Database (TCDB) Number 2.A.20) comprising conserved symporters throughout all kingdoms that use either sodium or proton gradients to transport Pi. In mammals, the PiT family is comprised of only two members, PiT1 (SLC20A1) and PiT2 (SLC20A2), which were initially identified as receptors for retroviruses and were subsequently found to possess electrogenic $Na^+$-Pi symporter activity. Due to the requirement of large amounts of Pi in bone physiology, the regulation of PiT1 has been well documented in bone and cartilage in vitro models. In osteoblast-like cells, PiT1, but not PiT2, mRNA expression and Na+-Pi cotransport are regulated by various factors such as Pi, epinephrine, insulin-like growth factor 1 (IGF-1), and bone morphogenic protein 2 (BMP2). Importantly, PiT1, but not PiT2 is upregulated during osteoblast differentiation, consistent with a dedicated role of PiT1 in this process. Expression and activity of PiT1 in chondrogenic cells was found to be regulated by extracellular Pi concentration and transforming growth factor-$\beta$ (TGF-$\beta$). Moreover, vascular calcification occurring in pathological situations such as hyperphosphatemia-induced calcifications of blood vessels and osteoarthritis, shares a number of similarities with osteogenesis and bone mineralization. Recent in vitro studies have suggested that PiT1 may be implicated in pathological vascular calcification. Particularly, inhibition of Pi uptake by PiT1 small hairpin RNA in cultured vascular smooth muscle cells (VSMCs) blocked the expression of Pi-induced osteogenic differentiation markers, Runx2 and osteopontin, indicating that PiT1 might be a major mechanism for controlling vascular calcification and VSMC phenotypic state.

However, it should be noted that the above-mentioned studies have been conducted in in vitro models and it is not clear which role PiT1 plays in normal bone or vascular physiology. Particularly, the discrete expression of PiT1 in a subset of hypertrophic chondrocytes late in development, its weak expression in osteoblasts and VSMCs together with its low transport capacity make it an unlikely candidate to face the tremendous Pi needs for bone or vascular calcification. Moreover, since most studies aimed at elucidating PiT1 regulation and function were conducted in tissues in which Pi per se plays an important role (i.e. mineralized tissues), very little information is available for other tissues. Since PiT1 is expressed in numerous non-mineralizing tissues, it is entirely possible that PiT1 possesses regulated tissue-specific roles going beyond a housekeeping $Na^+$-Pi transport function.

Cancer is a class of diseases in which a group of cells display uncontrolled growth (division beyond the normal limits), invasion (intrusion on and destruction of adjacent tissues), and sometimes metastasis (spread to other locations in the body via lymph or blood). Cancer is a generic term for a large group of diseases that can affect any part of the body and is a leading cause of death worldwide. The disease accounted for 7.4 million deaths (or around 13% of all deaths worldwide) in 2004 and deaths from cancer worldwide are projected to continue rising, with an estimated 12 million deaths in 2030 according the World Health Organization. The main types of cancer leading to overall cancer mortality each year are lung cancer, stomach cancer, colorectal cancer, breast cancer and liver cancer.

Amongst liver cancer, the most frequent is hepatocellular carcinoma (HCC) (also named hepatoma). Liver cancer is a fairly rare form of cancer in the western world (1% of all cancers) but much more common in Africa and parts of Asia (10% to 50% of all cancers). Having certain diseases may lead to liver cancer. These include cirrhosis of the liver, chronic alcoholism, chronic hepatitis C and chronic hepatitis B. People at risk for developing liver cancer also include those who are obese or have diabetes. Liver cancer is much more prevalent in men and incidence increases with age. This cancer is rapidly fatal, usually within 6 months from gastrointestinal hemorrhage, hepatic failure or metastasis.

It should be noted that liver cancer is most curable if caught in the earliest stage of the disease. However, there are generally no symptoms in early stages of liver cancer. If there are symptoms, they can be very vague and include nausea, weight loss, and loss of appetite. Therefore, a diagnosis of liver cancer can be missed or delayed because there are generally no symptoms in early stages of the disease.

However, as discussed above most solid tumors, including liver cancer, can often be cured only if they are detected and treated at an early stage.

Thus, there is still an existing need to develop a method for diagnosing cancer, notably liver cancer and more particularly during early-stage of liver cancer development.

There is also an urgent need to develop a method for prevention or treating cancer in particular liver cancer such as hepatocellular carcinoma.

SUMMARY OF THE INVENTION

The invention relates to a method for detecting/diagnosing a cancer and/or metastases in a patient comprising the step of determining the expression level of the phosphate transporter PiT1 gene in a biological sample obtained from said patient.

The invention further relates to a method for staging a cancer in a patient having cancer comprising the step of determining the expression level of the PiT 1 gene in a biological sample obtained from said patient.

The invention further relates to a method for screening an asymptomatic patient at risk for cancer, said method comprising the step of determining the expression level of the PiT1 gene in a biological sample obtained from said patient.

The method further relates to a method of detecting and localizing cancer cells and/or metastases stemming from cancer cells in the body of a patient, to which a quantity sufficient for imaging of a labelled agent which binds to PiT1 has been previously administered, comprising the step of subjecting said body to imaging.

The invention further relates to a method for preventing or treating a cancer in a patient, comprising the step of administrating an effective amount of an inhibitor of the activation of the PiT1 to a subject in need thereof.

The invention further relates to a method for screening a drug for the prevention or the treatment of cancer.

Preferably the cancer is a liver cancer, most preferably a hepatocellular carcinoma (HCC).

The invention further relates to compositions and kit for performing the methods described above.

DETAILED DESCRIPTION OF THE INVENTION

The inventors made the observation that PiT1 may be used for an early and accurate detection of cancer, including liver cancer (such as hepatocellular carcinoma) since PiT1 is massively and selectively overexpressed in liver carcinoma nodules.

Moreover, PiT1 may be used as a new target for the prevention or the treatment of cancer including liver cancer since inhibition of PiT1 leads to a significant decrease of the proliferation of tumor cells, in particular HepG2 cells. Importantly, the inventors also showed that this property was not shared with PiT2, whose depletion had no effect on proliferation.

DEFINITIONS

Throughout the specification, several terms are employed and are defined in the following paragraphs.

The term "PiT1", as used herein, is intended to encompass all synonyms including, but not limited to, SLC20A1 and GLVR1. The term "PiT1" thus includes naturally occurring PiT1 and variants and modified forms thereof. For example, the naturally occurring human PiT1 gene has a nucleotide sequence shown in Genbank Accession number NP_005406 and the naturally occurring human protein has an amino acid sequence shown in Genbank Accession number NM_005415.

As used herein, the terms "PiT1-specific binding molecule" or "binding partner capable of selectively interacting with PiT1" intended to refer to a molecule of sufficient size and complexity so as to be capable of selectively binding PiT1.

The term "anti-PiT1 antibody" refers to an antibody or a fragment thereof which selectively recognizes PiT1. As used herein, the term "antibody" refers to a protein capable of specifically binding an antigen, typically and preferably by binding an epitope or antigenic determinant or said antigen. The term "antibody" also includes recombinant proteins comprising the binding domains, as well as variants and fragments of antibodies. Examples of fragments of antibodies include Fv, Fab, Fab', F(ab')2, dsFv, scFv, sc(Fv)2, diabodies and multispecific antibodies formed from antibody fragments.

The term "a polypeptide corresponding to the envelope proteins of GALV (Gibbon Ape Leukemia Virus) or of FeLV-B (Feline Leukemia Virus B) or derivatives thereof" refers to a polypeptide selected for its ability to bind specifically to PiT1. During the process of infection, the SU domain is required for interaction with the respective receptor while the TM domain is responsible for subsequent fusion of the virus particle with the interacting cell. More particularly, the SU domain contains two major domains: a domain of interaction with the TM domain and the receptor binding domain (RBD), RBD being liable to interact with host cell membrane receptor and therefore to form a complex with said receptor.

Thus, in the context of the present invention, RBD are found in the glycoprotein of the envelope of GALV, therefore, the polypeptide corresponding to the envelope proteins of GALV or derivatives thereof contains at least the total RBD or a fragment thereof said fragment or totality of RBD being liable to interact with PiT1.

For instance, such polypeptide may comprise the amino-terminal SU (surface) domain of the envelope protein of GALV as described in Kurre et al. 2001.

Another polypeptide useful in the context of the present invention is for instance described in the international Patent Application WO 2010/079208, which is included herein by reference. Said international patent describes a polypeptide (also called receptor binding ligand) which is isolated from the soluble part of the glycoprotein of the enveloped virus GALV and that interacts with the cellular cognate receptor PiT1.

It should be further noted that the polypeptide according to the invention containing part or the totality of the RBD may be chemically modified to add a label such as a fluorochrome, a radioactive isotope or a paramagnetic agent.

In a particular embodiment, the polypeptide corresponding to the envelope proteins of GALV or derivatives thereof" is the polypeptide represented by SEQ ID NO: 1.

As used herein, the term "derivatives" includes the variants and the fragments of the polypeptide to which it refers (i.e. glycoprotein of the enveloped virus GALV) and that retain the biological activity and the specificity of the parent polypeptide (i.e. its ability to bind specifically to PiT1).

As used herein, references to a specific gene (e.g., Env gene of GALV) may include a nucleic acid having a native (endogenous) polynucleotide sequence or any allelic or polymorphic variant thereof, as well as the orthologous sequences found in other species. Polynucleotide variants may contain one or more substitutions, additions, deletions and/or insertions. For example, due to the inherent degeneracy of the genetic code, other DNA sequences that encode substantially the same or a functionally equivalent amino acid sequence may be produced and these sequences may be used to clone and express a given polypeptide.

As used herein, references to specific protein (e.g., envelope glycoprotein) may include a polypeptide having a native amino acid sequence, as well as variants and modified forms regardless of their origin or mode of preparation. A protein that has a native amino acid sequence is a protein having the same amino acid sequence as obtained from nature (e.g., a naturally occurring envelope protein). Such native sequence proteins may be isolated from nature or can be prepared using standard recombinant and/or synthetic methods. Native sequence proteins specifically encompass naturally occurring truncated or soluble forms, naturally occurring variant forms naturally occurring allelic variants and forms including post-translational modifications. A native sequence protein includes proteins following post-translational modifications such as glycosylation, or phosphorylation, ubiquitination, sumoylation or other modifications of some amino acid residues.

Variants refer to proteins that are functional equivalents to a native sequence protein that have similar amino acid sequences and retain, to some extent, one or more activities of the native protein. Variants also include fragments that retain activity. Variants also include proteins that are substantially identical (e.g., that have 80, 85, 90, 95, 97, 98, 99%, sequence identity) to a native sequence. Such variants include proteins having amino acid alterations such as deletions, insertions and/or substitutions. A "deletion" refers to the absence of one or more amino acid residues in the related protein. The term "insertion" refers to the addition of one or more amino acids in the related protein. A "substitution" refers to the replacement of one or more amino acid residues by another amino acid residue in the polypeptide. Typically, such alterations are conservative in nature such that the activity of the variant protein is substantially similar to a native sequence protein.

As used herein, the term "cancer" refers to the physiological condition in mammals that is typically characterized by unregulated cell growth.

Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer ("NSCLC"), adenocarcinoma of the lung and squamous carcinoma of the lung, cancer of the peritoneum, gastric or stomach cancer including gastrointestinal cancer, pancreatic cancer, glioblastoma, cervical cancer, ovarian cancer, liver cancer, bladder cancer, breast cancer, colon cancer, rectal cancer, colorectal cancer, endometrial or uterine carcinoma, salivary gland carcinoma, kidney or renal cancer, prostate cancer, vulval cancer, thyroid cancer, anal carcinoma, penile carcinoma, as well as head and neck cancer.

As used herein, the term "liver cancer" refers to liver carcinomas notably hepatocellular carcinoma (HCC)) as well as other tumors of liver (e.g., cholangiocarcinoma (bile duct cancers), combined hepatocellular carcinoma and cholangiocarcinoma, and hepatoblastoma).

The term "metastases" has its general meaning in the art and refers to the spread of a tumor from an organ to another non-adjacent organ or part.

The term "liver metastases" has its general meaning in the art and refers to the spread of a tumor from liver to another non-adjacent organ or part such as the lungs for instance.

The term "determining" as used herein includes qualitative and/or quantitative detection (i.e. detecting and/or measuring expression level) with or without reference to a control or a predetermined value. As used herein, "detecting" means determining if PiT1 is present or not in a biological sample and "measuring" means determining the amount of PiT1 in a biological sample. Typically PiT1 level expression may be determined for example by RT-PCR or immunohistochemistry (IHC) performed on a liver sample obtained by biopsy. Alternatively, levels of PiT1 in whole blood sample, plasma sample or serum sample obtained from the subjects may be determined.

Preferably, the sample is a whole blood sample.

As used herein, the term "predetermined value" refers to the amount of PiT1 in biological samples obtained from the general population or from a selected population of subjects. The predetermined value can be a threshold value or a range. For example, the selected population may be comprised of apparently healthy subjects, such as individuals who have not previously had any sign or symptoms indicating the presence of a cancer such as a liver cancer. In another example, the predetermined value may be of the amount of PiT1 obtained from subjects having an established cancer such as a liver cancer. The predetermined value may be established based upon comparative measurements between apparently healthy subjects and subjects with established cancer such as a liver cancer.

The term "patient" or "subject" as used herein denote a mamma such as a rodent, a feline, a canine, and a primate. Preferably, a patient according to the invention is a human.

The term "healthy subjects" as used herein refers to a population of subjects who do not suffer from any known condition, and in particular, who are not affected with a cancer such as a liver cancer (e.g. a hepatocellular carcinoma (HCC)).

The term "biological sample" means any biological sample derived from a patient. Examples of such samples include tissues, cell samples, cell lysates, biopsies, etc. Preferred biological samples are a tumor sample or a biopsy such as liver tumor sample. Other biological samples are whole blood, serum or plasma. Preferably, the sample is a whole blood sample The term "biomarker", as used herein, refers generally to a molecule, i.e., a gene (or nucleic acid encoding said gene), protein, the expression of which in a biological sample from a patient can be detected by standard methods in the art (as well as those disclosed herein), and is predictive or denotes a condition of the patient from which it was obtained.

Diagnostic Methods and Kits

The present invention relates to a method for detecting cancer and/or metastases in a patient comprising determining the expression level of the PiT1 gene in a biological sample obtained from said patient.

In an embodiment, the biological sample is a tumor sample.

In a particular embodiment, the invention relates to a method for detecting liver cancer and/or liver metastases in a patient comprising determining the expression level of the PiT1 gene in a biological sample obtained from said patient.

In another particular embodiment, the biological sample is a liver tumor sample.

In still another particular embodiment, the patient is affected with a hepatocellular carcinoma (HCC).

In an embodiment, the method of the invention further may comprise a step of comparing the quantity of mRNA encoding PiT1 with a predetermined threshold value. Said comparison is indicative of liver cancer. PiT1 is indeed increased during the development of liver cancer and notably during early-stage of liver cancer development.

Accordingly a further aspect of the invention relates to a method for detecting liver cancer and/or liver metastases in a patient, said method comprising the steps of:

(i) determining the quantity of mRNA encoding PiT1 in a biological sample obtained from said patient, (ii) comparing the quantity of mRNA encoding PiT1 measured in step (i) to a reference value derived from the quantity of mRNA encoding PiT1 in a biological sample from a subject who does not suffer from liver cancer, wherein an elevated level of PiT1 in the biological sample obtained from said patient as compared to said reference value indicates that the patient suffers from a liver cancer.

The present invention also relates to a method for staging a cancer in a patient having a cancer comprising determining the expression level of the PiT1 gene in a biological sample obtained from said patient.

In an embodiment, the biological sample is a tumor sample.

In an embodiment, the invention relates to a method for staging a liver cancer in a patient having a liver cancer comprising determining the expression level of the PiT1 gene in a biological sample obtained from said patient.

Accordingly in a particular embodiment, the biological sample is a liver tumor sample.

In another particular embodiment, the patient is affected with a hepatocellular carcinoma (HCC).

The present invention further relates to a method for screening an asymptomatic patient at risk for cancer, said method comprising the step of determining the expression level of the PiT1 gene in a biological sample obtained from said patient.

In an embodiment, the biological sample is a tumor sample.

In an embodiment, the invention relates to a method for screening an asymptomatic patient at risk for liver cancer, said method comprising the step of determining the expression level of the PiT1 gene in a biological sample obtained from said patient.

Accordingly in a particular embodiment, the biological sample is a liver tumor sample.

In another particular embodiment, the patient is affected with a hepatocellular carcinoma (HCC).

The present invention further enables the evaluation of the risk of recurrence of a subject which has been surgically treated and subsequently received the appropriate treatment (such as radiotherapy and/or chemotherapy).

In another embodiment, the patient is affected with a hepatocellular carcinoma (HCC).

The present invention further relates to a method for monitoring a treatment of a patient affected by a liver cancer and/or liver metastases with a PiT1 antagonist comprising determining the expression level of the PiT1 gene in a biological sample obtained from said patient, and optionally, comparing the expression level of the PiT1 gene with a predetermined value representing a predetermined stage of the liver cancer, the expression level of the PiT1 gene with respect to the predetermined value indicating the evolution of the liver cancer, and therefore the degree of efficacy of the treatment.

In an embodiment, the biological sample is a liver tumor sample.

In another embodiment, the patient is affected with a hepatocellular carcinoma (HCC).

Methods for Determining the Expression Level of the Genes of the Invention

Determination of the expression level of the PiT1 gene may be performed by a variety of techniques. Generally, the expression level as determined is a relative expression level.

For example, the determination comprises contacting the biological sample with selective reagents such as probes, primers or ligands, and thereby detecting the presence, or measuring the amount, of polypeptide or nucleic acids of interest originally in said biological sample. Contacting may be performed in any suitable device, such as a plate, microtiter dish, test tube, well, glass, column, and so forth. In specific embodiments, the contacting is performed on a substrate coated with the reagent, such as a nucleic acid array or a specific ligand array. The substrate may be a solid or semisolid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or polypeptides of the biological sample.

In a particular embodiment, the expression level may be determined by determining the quantity of mRNA.

Methods for determining the quantity of mRNA are well known in the art. For example the nucleic acid contained in the biological samples (e.g., cell or tissue prepared from the patient) is first extracted according to standard methods, for example using lytic enzymes or chemical solutions or extracted by nucleic-acid-binding resins following the manufacturer's instructions. The extracted mRNA is then detected by hybridization (e.g., Northern blot analysis) and/or amplification (e.g., RT-PCR). Quantitative or semi-quantitative RT-PCR is preferred. Real-time quantitative or semi-quantitative RT-PCR is particularly advantageous.

Other methods of Amplification include ligase chain reaction (LCR), transcription-mediated amplification (TMA), strand displacement amplification (SDA) and nucleic acid sequence based amplification (NASBA).

Nucleic acids having at least 10 nucleotides and exhibiting sequence complementarily or homology to the mRNA of interest herein find utility as hybridization probes or amplification primers. It is understood that such nucleic acids need not be identical, but are typically at least about 80% identical to the homologous region of comparable size, more preferably 85% identical and even more preferably 90-95% identical.

In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (e.g. avidin/biotin).

Probes typically comprise single-stranded nucleic acids of between 10 to 1000 nucleotides in length, for instance of between 10 and 800, more preferably of between 15 and 700, typically of between 20 and 500. Primers typically are shorter single-stranded nucleic acids, of between 10 to 25 nucleotides in length, designed to perfectly or almost perfectly match a nucleic acid of interest, to be amplified. The probes and primers are "specific" to the nucleic acids they hybridize to, i.e. they preferably hybridize under high stringency hybridization conditions (corresponding to the highest melting temperature Tm, e.g., 50% formamide, 5× or 6×SCC. SCC is a 0.15 M NaCl, 0.015 M Na-citrate).

The nucleic acid primers or probes used in the above detection, staging, screening and monitoring methods may be assembled as a kit. Such a kit includes consensus primers and molecular probes. A particular kit also includes the components necessary to determine if amplification has occurred. The kit may also include, for example, PCR buffers and enzymes; positive control sequences, reaction control primers; and instructions for amplifying and detecting the specific sequences.

Accordingly, the present invention also relates to a kit for performing a method above-mentioned, wherein said kit comprises means for determining the expression level of the PiT1 gene in a biological sample obtained from said patient.

In a particular embodiment, the methods of the invention comprise the steps of providing total RNAs extracted from a biological sample such a tumor sample or biopsy and subjecting the RNAs to amplification and hybridization to specific probes, more particularly by means of a quantitative or semi-quantitative RT-PCR.

In another particular embodiment, the expression level is determined by DNA chip analysis. Such DNA chip or nucleic acid microarray consists of different nucleic acid probes that are chemically attached to a substrate, which can be a microchip, a glass slide or a microsphere-sized bead. A microchip may be constituted of polymers, plastics, resins, polysaccharides, silica or silica-based materials, carbon, metals, inorganic glasses, or nitrocellulose. Probes comprise nucleic acids such as cDNAs or oligonucleotides that may be about 10 to about 60 base pairs. To determine the expression level, a biological sample from a test subject, optionally first subjected to a reverse transcription, is labelled and contacted with the microarray in hybridization conditions, leading to the formation of complexes between target nucleic acids that are complementary to probe sequences attached to the microarray surface. The labelled hybridized complexes are then detected and can be quantified or semi-quantified. Labelling may be achieved by various methods, e.g. by using radioactive or fluorescent labelling. Many variants of the microarray hybridization technology are available to the man skilled in the art (see e.g., Hoheisel, Nature Reviews, Genetics, 2006, 7:200-210).

In this context, the invention further provides a DNA chip comprising a solid support which carries nucleic acids that are specific to the PiT1 gene.

Other methods for determining the expression level of said genes include the determination of the quantity of proteins encoded by PiT1 gene.

Such methods comprise contacting the sample with a binding partner capable of selectively interacting with a marker protein present in the sample. The binding partner is generally an antibody that may be polyclonal or monoclonal, preferably monoclonal.

It should be further noted that the binding partner may also be an aptamer.

The presence of the protein of interest may be detected using standard electrophoretic and immunodiagnostic techniques, including immunoassays such as competition, direct reaction, or sandwich type assays. Such assays include, but are not limited to, Western blots; agglutination tests; enzyme-labelled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith. Labels are known in the art that generally provide (either directly or indirectly) a signal. As used herein, the term "labelled" with regard to the antibody or aptamer, is intended to encompass direct labelling of the antibody or aptamer by coupling (i.e., physically linking) a detectable substance, such as a radioactive agent or a fluorophore (e.g. fluorescein isothiocyanate (FITC) or phycoerythrin (PE) or indocyanine (Cy5), to the antibody or aptamer, as well as indirect labelling of the probe or antibody (e.g., horseradish peroxidise, HRP) by reactivity with a detectable substance. An antibody or aptamer may be also labelled with a radioactive molecule by any method known in the art. For example, radioactive molecules include but are not limited radioactive atom for scintigraphic studies such as I123, I124, In111, Re186 and Re188. The aforementioned assays generally involve separation of unbound protein in a liquid phase from a solid phase support to which antigen-antibody complexes are bound. Solid supports which may be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, etc.

More particularly, an ELISA method may be used, wherein the wells of a microtiter plate are coated with an antibody against the protein to be tested. A biological sample containing or suspected of containing the marker protein is then added to the coated wells. After a period of incubation sufficient to allow the formation of antibody-antigen complexes, the plate (s) can be washed to remove unbound moieties and a detectably labelled secondary binding molecule added. The secondary binding molecule is allowed to react with any captured sample marker protein, the plate washed and the presence of the secondary binding molecule detected using methods well known in the art.

Alternatively, an immunohistochemistry (IHC) method may be used. IHC specifically provides a method of detecting a target in a biological sample or tissue specimen in situ. The overall cellular integrity of the sample is maintained in IHC, thus allowing detection of both the presence and location of the target of interest. Typically a biological sample is fixed with formalin, embedded in paraffin and cut into sections for staining and subsequent inspection by light microscopy. Current methods of IHC use either direct labelling or secondary antibody-based or hapten-based labelling. Examples of known IHC systems include, for example, EnVision™ (DakoCytomation), Powervision® (Immunovision, Springdale, Ariz.), the NBA™ kit (Zymed Laboratories Inc., South San Francisco, Calif.), HistoFine® (Nichirei Corp, Tokyo, Japan).

In particular embodiment, a tissue section (e.g. a liver tumor sample or biopsy) may be mounted on a slide or other support after incubation with antibodies directed against the protein encoded by PiT1 gene. Then, microscopic inspections in the sample mounted on a suitable solid support may be performed. For the production of photomicrographs, sections comprising samples may be mounted on a glass slide or other planar support, to highlight by selective staining the presence of the protein of interest. Therefore IHC samples may include, for instance: (a) preparations comprising cell samples (b) fixed and embedded said cells and (c) detecting the protein of interest in said cell samples. In some embodiments, an IHC staining procedure may comprise steps such as: cutting and trimming tissue, fixation, dehydration, paraffin infiltration, cutting in thin sections, mounting onto glass slides, baking, deparaffination, rehydration, antigen retrieval, blocking steps, applying primary antibodies, washing, applying secondary antibodies (optionally coupled to a suitable detectable label), washing, counter staining, and microscopic examination.

The present invention also relates to a kit for performing the methods as above described, wherein said kit comprises means for determining the expression level PiT1 gene that is indicative whether the patient is affected by a cancer.

The present invention also provides a method of detecting and localizing cancer cells and/or metastases stemming from cancer cells in the body of a patient, to which a quantity sufficient for imaging of a labelled agent which binds to PiT1 has been previously administered, comprising the step of subjecting said body to imaging.

In a particular embodiment, the invention relates to a method of detecting and localizing liver cancer cells and/or metastases stemming from liver cancer cells in the body of a patient, to which a quantity sufficient for imaging of a labelled agent which binds to PiT1 has been previously administered, comprising the step of subjecting said body to imaging Examples of labelled agents which bind to PiT1 may be selected from the group consisting of a labelled antibody against PiT1 or a fragment thereof, a labelled aptamer against PiT1 or a labelled polypeptide corresponding to the envelope proteins of GALV (Gibbon Ape Leukemia Virus) or derivatives thereof.

In an embodiment, the labelled agent which binds to PiT1 is a labelled polypeptide corresponding to the envelope proteins of GALV or derivatives thereof.

In a particular embodiment, the labelled polypeptide corresponding to the envelope proteins of GALV or derivatives thereof is a polypeptide represented by SEQ ID NO: 1.

The present invention also relates to a labelled agent which binds to PiT1 for a diagnosis of cancer practised on a subject.

In an embodiment, the present invention relates to a labelled agent which binds to PiT1 for a diagnosis of liver cancer practised on a subject.

In a particular embodiment of the invention, the invention enables the diagnosis of liver cancer at a very early stage of the disease such as at stage I (when the tumor is well localized and can be surgically removed).

Typically the present invention provides a method of detecting and localizing hepatic carcinoma nodules in situ.

It falls within the ability of the skilled artisan to carry out such an imaging method. Typically the label may be a fluorophore, a radioactive isotope or a paramagnetic agent. Depending on the label used, different imaging techniques may be used such as a chest x-ray, mammograms, bone scans, computed tomography (CT) scans, magnetic resonance imaging (MRI), positron emission tomography (PET) scans, or PET/CT.

A further aspect of the invention relates to the use of PiT1 as a biomarker of cancer such as liver cancer (including hepatocellular carcinoma (HCC)), in a patient.

A further aspect of the invention relates to the use of a kit detecting PiT1 for diagnosing cancer such as liver cancer in a patient.

Therapeutic Methods of the Invention

The invention also relates to a method for preventing or treating a cancer in a patient, comprising the step of administrating an effective amount of an inhibitor of the activation of the PiT1 to a subject in need thereof.

In another embodiment, the cancer is a cervical cancer.

In another embodiment, the cancer is a liver cancer.

In a particular embodiment, the patient is affected with a hepatocellular carcinoma (HCC).

The expression "inhibitors of the activation of PiT1" should be understood broadly, this expression refers to agents down-regulating the expression of PiT 1, compounds that bind to PiT 1 and inhibit the activation of PiT1.

Examples of inhibitors of the activation of PiT1 may be selected from the group consisting of an agent down-regulating the expression of PiT1, an antibody against PiT1 or a fragment thereof which binds to PiT 1 and an antagonist of PiT1.

In an embodiment, the inhibitor of the activation of PiT1 is an agent down-regulating the expression of PiT1 in cancer cells, in particular liver cancer cells.

Typically, agent down-regulating the expression of PiT1 comprises a nucleic acid which interferes with the expression of PiT1. Examples of such agents are antisense molecules or vectors comprising said antisense molecules. Antisense molecules are complementary strands of small segments of mRNA. Methods for designing effective antisense molecules being well known (see for example U.S. Pat. No. 6,165,990), it falls within the ability of the skilled artisan to design antisense molecules able to downregulate the expression of PiT1 in cancer cells, in particular in liver cancer cells. Further examples are RNA interference (RNAi) molecules such as, for example, short interfering RNAs (siRNAs) and short hairpin RNAs (shRNAs). RNAi refers to the introduction of homologous double stranded RNA to specifically target a gene's product, in the present case PiT1, resulting in a null or hypomorphic phenotype. Methods for designing effective RNAi molecules being well known (e.g., see for review Hannon and Rossi (2004) Nature September 16; 431(7006):371-8), it falls within the ability of the skilled artisan to design RNAi molecules able to downregulate the expression of PiT1 in cancer cells, in particular liver cancer cells.

Examples of siRNAs able to downregulate the expression of PiT1 are represented by SEQ ID NO: 2 (PiT1 siRNA-A) and SEQ ID NO: 3 (SEQ ID NO: 3).

In another embodiment of the invention, the inhibitor of the activation of PiT1 is an antibody against PiT1 or a fragment thereof.

The person skilled in the art will be aware of standard methods for production of such specific antibody or fragment thereof. For example, specific antibodies or fragment thereof may be generated by immunizing an animal with PiT1 and by selecting the antibodies which inhibit the activation of the PiT1.

The person skilled in the art will be aware of standard methods for production of both polyclonal and monoclonal antibodies and fragments thereof which binds to PiT1. Antibody fragments, particularly Fab fragments and other fragments which retain epitope-binding capacity and specificity are also well known, as are chimeric antibodies, and "humanized" antibodies, in which structural (not determining specificity for antigen) regions of the antibody are replaced with analogous or similar regions from another species. Thus, antibodies generated in mice can be "humanized" to reduce negative effects which may occur upon administration to human subjects. Chimeric antibodies are now accepted therapeutic modalities with several now on the market. The present invention therefore comprehends use of antibody specific for PiT1 which include $F(ab')_2$, $F(ab)_2$, Fab, Fv and Fd antibody fragments, chimeric antibodies in which one or more regions have been replaced by homologous human or non-human portions. The person skilled in the art will also be aware that fragments such as for example sdAb, ScFv fragments and divalent ScFv-type molecules can be prepared using recombinant methods.

In a further embodiment of the present invention, the inhibitor of the activation of PiT1 is an antagonist of PiT1.

The inhibitors of the activation of PiT1 may also be used in combination with other therapeutically active agents, for instance, cytotoxic agents and pro-apoptotic drugs.

In a particular embodiment, the cytotoxic agent is Tumor Necrosis Factor alpha (TNFα).

In another particular embodiment, the pro-apoptotic drug is an inhibitor of the NF-κB pathway. An inhibitor of the NF-κB pathway may be a biological or chemical compound which inhibits NF-kB or activation of the pathway. Such compound may be an inhibitor of the activation of NF-κB, a proteasome or a protease inhibitor that inhibits Rel/NF-kB or an IkBa phosphorylation and/or degradation inhibitor.

For instance, the NFkB inhibitor is selected from the group consisting of sulfasalazine, rapamycin, caffeic acid phenethylester, SN50 (a cell-permeable inhibitory peptide), parthenolide, triptolide, wedelolactone, lactacystin and MG-132.

The overexpression of PiT1 by cancer cells and in particular liver cancer cells enables the specific targeting of cancer cells and in particular liver cancer cells with cytotoxic agent which binds to the PiT1. Thus, the invention relates to a PiT1-specific binding molecule that may be used as a targeting tumor agent to deliver radioisotopes, chemotherapy or other cytotoxic agents (i.e. TNFα) to the tumour, in particular liver tumor.

Accordingly, the present invention provides thus a method for preventing or treating a cancer in a patient, comprising the step of administering an effective amount of a PiT1-specific binding molecule conjugated to a chemotherapeutic agent to a patient in need thereof.

Also provided is a PiT1-specific binding molecule conjugated to a chemotherapeutic agent for the prevention or the treatment of cancer.

In another embodiment, the cancer is a cervical cancer.

In another embodiment, the cancer is a liver cancer.

In a particular embodiment, the patient is affected with a hepatocellular carcinoma (HCC).

Examples of PiT1-specific binding molecule conjugated to a chemotherapeutic agent include an antibody against PiT1 or a fragment thereof which binds to PiT1, an aptamer or a polypeptide corresponding to the envelope proteins of GALV (Gibbon Ape Leukemia Virus), or a derivative thereof.

In the context of the invention, the term "treating" or "treatment", as used herein, means reversing, alleviating, inhibiting the progress of, or preventing the disorder or condition to which such term applies, or reversing, alleviating, inhibiting the progress of, or preventing one or more symptoms of cancer, such as liver cancer (e.g. (HCC)).

By a "therapeutically effective amount" of an inhibitor of activation of PiT1 or of a PiT1-specific binding molecule conjugated to a chemotherapeutic agent is meant a sufficient amount to treat cancer, in particular liver cancer, at a reasonable benefit/risk ratio applicable to any medical treatment. It will be understood, however, that the total daily usage of the inhibitor or of the chemotherapeutic agent will be decided by the attending physician within the scope of sound medical judgment. The specific therapeutically effective dose level for any particular subject in need thereof will depend upon a variety of factors including the stage of liver cancer being treated and the activity of the specific inhibitor/chemotherapeutic agent employed, the age, body weight, general health, sex and diet of the subject, the time of administration, route of administration, the duration of the treatment; drugs used in combination or coincidental with the and like factors well known in the medical arts. For example, it is well known within the skill of the art to start doses of the compound at levels lower than those required to achieve the desired therapeutic effect and to gradually increase the dosage until the desired effect is achieved. Typically medicaments according to the invention comprise an inhibitor of the activation of PiT1 or a PiT1-specific binding molecule conjugated to a chemotherapeutic agent, together with a pharmaceutically-acceptable carrier. A person skilled in the art will be aware of suitable carriers. Suitable formulations for administration by any desired route may be prepared by standard methods, for example by reference to well-known text such as Remington; The Science and Practice of Pharmacy.

According to the invention, said PiT1-specific binding molecule is conjugated to a chemotherapeutic agent A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy. Examples of chemotherapeutic agents include: erlotinib (TARCEVA®, Genentech/OSI Pharm.), docetaxel (TAXOTERE®, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL®, Bristol-Myers Squibb Oncology, Princeton, N.J.), trastuzumab (HERCEPTIN®, Genentech), temozolomide (4-methyl-5-oxo-2,3,4,6,8-pentazabicyclo[4.3.0]nona-2,7,9-triene-9-carboxamide, CAS No. 85622-93-1, TEMODAR®, TEMODAL®, Schering Plough), tamoxifen ((Z)-2-[4-(1,2-diphenylbut-1-enyl)phenoxy]-N,N-dimethyl-ethanamine, NOLVADEX®, ISTUB AL®, Conjugation of the PiT1-specific binding molecule of the invention with chemotherapeutic agents may be made using a variety of bifunctional protein coupling agents including but not limited to N-succinimidyl(2-pyridyldithio)propionate (SPDP), succinimidyl(N-maleimidomethyl)cyclohexane-1-carboxylate, iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as tolyene 2,6diisocyanate), and bis-active fluorine compounds (such as 1,5-difluoro-2,4-dinitrobenzene).

The linker may be a "cleavable linker" facilitating release of the cytotoxic agent or growth inhibitory agent in the cell. For example, an acid-labile linker, peptidase-sensitive linker, photolabile linker, dimethyl linker or disulfide-containing linker (See e.g. U.S. Pat. No. 5,208,020) may be used.

Pharmaceutical Compositions

The inhibitor of activation of PiT1 or of a PiT1-specific binding molecule conjugated to a chemotherapeutic agent may be combined with pharmaceutically acceptable excipients, and optionally sustained-release matrices, such as biodegradable polymers, to form therapeutic compositions.

In the pharmaceutical compositions of the present invention, the active principle, alone or in combination with another active principle, can be administered in a unit administration form, as a mixture with conventional pharmaceutical supports, to animals and human beings. Suitable unit administration forms comprise oral-route forms such as tablets, gel capsules, powders, granules and oral suspensions or solutions, sublingual and buccal administration forms, aerosols, implants, subcutaneous, transdermal, topical, intraperitoneal, intramuscular, intravenous, subdermal, transdermal, intrathecal and intranasal administration forms and rectal administration forms.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions comprising compounds of the invention as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The inhibitor of activation of PiT1 or of a PiT1-specific binding molecule conjugated to a chemotherapeutic agent of the invention may be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active polypeptides in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion. Some variation in dosage will necessarily occur depending on the condition of the subject being treated. The person responsible for administration will, in any event, determine the appropriate dose for the individual subject.

The inhibitor of activation of PiT1 or of a PiT1-specific binding molecule conjugated to a chemotherapeutic agent of the invention may be formulated within a therapeutic mixture to comprise about 0.0001 to 1.0 milligrams, or about 0.001 to 0.1 milligrams, or about 0.1 to 1.0 or even about 10 milligrams per dose or so. Multiple doses can also be administered.

In addition to the compounds of the invention formulated for parenteral administration, such as intravenous or intramuscular injection, other pharmaceutically acceptable forms include, e.g. tablets or other solids for oral administration; liposomal formulations; time release capsules; and any other form currently used.

Screening Methods

A further aspect of the invention relates a method for screening a PiT1 antagonist for the treatment or prevention of cancer, in particular liver cancer.

For example, the screening method may measure the binding of a candidate compound to PiT1, or to cells or membranes bearing Pit1, or a fusion protein thereof by means of a label directly or indirectly associated with the candidate compound.

In a particular embodiment, the screening method of the invention comprises the steps consisting of:

a) providing a plurality of cells expressing PiT1 on their surface;
b) incubating said cells with a candidate compound;
c) determining whether said candidate compound binds to and inhibits PiT1; and
d) selecting the candidate compound that binds to and inhibits PiT1.

In a particular embodiment, the screening method of the invention may further comprising a step consisting of administering the candidate compound selected at step d) to an animal model of cancer, in particular an animal model of liver cancer to validate the therapeutic and/or protective effects of said candidate compound on cancer.

In one particular embodiment, the PiT1 antagonist is a selective PiT1 antagonist.

In general, such screening methods involve providing appropriate cells which express PiT1 on their surface. In particular, a nucleic acid encoding PiT1 may be employed to transfect cells to thereby express the receptor of the invention. Such a transfection may be accomplished by methods well known in the art.

In a particular embodiment, said cells may be selected from the group consisting of the mammal cells reported yet to express PiT1 (e.g. Hela cells Hepa RG cells, HuH7 cells or HepG2 cells).

The screening method of the invention may be employed for determining an antagonist by contacting such cells with compounds to be screened and determining whether such compound inhibits PiT1.

According to an embodiment of the invention, the candidate compounds may be selected from a library of compounds previously synthesised, or a library of compounds for which the structure is determined in a database, or from a library of compounds that have been synthesised de novo or natural compounds.

The candidate compound may be selected from the group of (a) proteins or peptides, (b) nucleic acids and (c) organic or chemical compounds (natural or not).

Such the method may be used to screen PiT1 antagonist according to the invention.

Methods of Inducing Proliferation of Somatic Cells:

The invention also relates to a method for inducing proliferation of somatic cells comprising a step of activating expression of PiT1 in said cells or contacting said cells with PiT1 protein.

For example, the somatic cells are selected in the group consisting of epidermal cells, epithelial cells, keratinocytes, neurons (including motor neurons, specific neurotransmitter producing neurons such as dopaminergic neurons), glia cells, retinal cells, lens cells of the cornea, hair cells of the inner ear, chondrocytes, chondroblasts, pancreatic endocrine cells (including endocrine pancreatic cells such as pancreatic beta cells), hepatocytes, endothelial cells, hematopoietic cells (including erythrocytes, lymphocytes (including B, T and NK lymphocytes), monocytes, macrophages and dendritic cells), cardiac muscle cells and other muscle cells, skeletal myocytes, osteoblasts and osteoclasts.

In a particular embodiment, the somatic cells are hepatocytes.

The somatic cells thus obtained may have various uses.

Said somatic cells may be suitable for therapy and/or reconstruction or regeneration.

For instance, hepatocytes may be used for hepatic therapy and/or hepatic reconstruction or regeneration.

Therefore a related aspect of the invention concerns a pharmaceutical composition comprising a population of somatic cells such as hepatocytes of the invention and optionally a pharmaceutically acceptable carrier or excipient.

In certain embodiments, a pharmaceutical composition may further comprise at least one biologically active substance or bioactive factor.

As used herein, the term "pharmaceutically acceptable carrier or excipient" refers to a carrier medium which does not interfere with the effectiveness of the biological activity of the progenitor cells, and which is not excessively toxic to the host at the concentrations at which it is administered. Examples of suitable pharmaceutically acceptable carriers or excipients include, but are not limited to, water, salt solution (e.g., Ringer's solution), oils, gelatines, carbohydrates (e.g., lactose, amylase or starch), fatty acid esters, hydroxymethylcellulose, and polyvinyl pyroline. Pharmaceutical compositions may be formulated as liquids, semi-liquids (e.g., gels) or solids (e.g., matrix, lattices, scaffolds, and the like).

As used herein the term "biologically active substance or bioactive factor" refers to any molecule or compound whose presence in a pharmaceutical composition of the invention is beneficial to the subject receiving the composition. As will be acknowledged by one skilled in the art, biologically active substances or bioactive factors suitable for use in the practice of the present invention may be found in a wide variety of families of bioactive molecules and compounds. For example, a biologically active substance or bioactive factor useful may be selected from anti-inflammatory agents, anti-apoptotic agents, immunosuppressive or immunomodulatory agents, antioxidants, growth factors, and drugs.

Another related aspect of the invention concerns a method for treating a subject suffering from a pathology such as a hepatic pathology, said method comprising a step of administering to the subject an efficient amount of a population of hepatocytes obtained according to the invention (or a pharmaceutical composition thereof).

In a particular embodiment, the method is useful for treating a subject suffering from a hepatic pathology, said method comprising a step of administering to the subject an efficient amount of a population of hepatocytes obtained according to the invention (or a pharmaceutical composition thereof).

According to this particular embodiment, the hepatic pathology which may be treated is selected in the group consisting of inherited metabolic disorders (such as Crigler-Najjar Syndrome type I, glucogenosis 1a, OTC deficiency, familial hypercholesterolemia and tyrosinemia), chronic or acute liver failure which may be caused by viral infection (in particular infection with HBV or HCV), toxic (alcohol) and drugs, metabolic diseases (Non-Alcoholic Fatty Liver Disease, Haemochromatosis, Wilson's Disease) or autoimmune disorder (Autoimmune Chronic Hepatitis, Primary Biliary Cirrhosis, Primary Sclerosing Cholangitis).

As used herein, the term "efficient amount" refers to any amount of a population of hepatic progenitor cells derived from definitive endoderm cells (or a pharmaceutical composition thereof) that is sufficient to achieve the intended purpose.

The population of hepatocytes (or a pharmaceutical composition thereof) of the invention may be administered to a subject using any suitable method.

The hepatocytes of the invention may be implanted alone or in combination with other cells, and/or in combination with other biologically active factors or reagents, and/or drugs. As will be appreciated by those skilled in the art, these other cells, biologically active factors, reagents, and drugs may be administered simultaneously or sequentially with hepatocytes.

In certain embodiments, a treatment according to the invention further comprises pharmacologically immunosuppressing the subject prior to initiating the cell-based treatment. Methods for the systemic or local immunosuppression of a subject are well known in the art.

Effective dosages and administration regimens can be readily determined by good medical practice based on the nature of the pathology of the subject, and will depend on a number of factors including, but not limited to, the extent of the symptoms of the pathology and extent of damage or degeneration of the tissue or organ of interest, and characteristics of the subject (e.g., age, body weight, gender, general health, and the like).

Other uses of somatic cells also include, but are not limited to, use for modelling injuries or pathologies such as injuries or pathologies associated with hepatic damage and for screening compounds in rodents.

For instance, hepatocytes may be used for a variety of in vitro and in vivo tests. In particular but in non limiting way, they find use in the evaluation of hepatotoxicity of compounds such as pharmaceutical candidate compounds.

Thus, a further aspect of the invention relates to a method for screening compounds having a hepatoprotective or hepatotoxic effect wherein said method comprises the steps of:
a. culturing a population of hepatocytes according to the invention in the presence of a test compound, and
b. comparing the survival of the cells of step a) to that of a population of said cells as defined above cultured in the absence of said test compound.

The term "hepatotoxic" refers to a compound which provokes a decrease in the survival of hepatic progenitor cells or hepatocytes. A compound is deemed to have a hepatotoxic effect if the number of viable cells cultured in the presence of said compound is lower than the number of viable cells cultured in the absence of said compound. The term "hepatoprotective" refers to a compound which results in an increase survival of hepatic progenitor cells or neurons. A compound is deemed to have a hepatoprotective effect if the number of viable cells cultured in the presence of said compound is higher than the number of viable cells cultured in the absence of said compound. Typically, the hepatoprotective effect can be assayed in the absence of hepatotrophic factors. Alternatively, the hepatoprotective effect can be assayed in the presence of a known hepatotoxic drug. Known hepatotoxic drugs include, but are not limited to amiodarone, methotrexate and nitrofurantoin.

Alternatively, biological or chemical compounds mimicking PiT1 protein activity may be used for inducing proliferation of somatic cells.

Alternatively, biological or chemical compounds inducing expression of PiT1 gene may be used for inducing proliferation of somatic cells.

The invention will be further illustrated by the following figures and examples. However, these examples and figures should not be interpreted in any way as limiting the scope of the present invention.

FIGURES

FIG. 1: PiT1, the major Pi transporter in HeLa cells, is critical for cell proliferation. A, relative levels of $Na^+$-Pi cotransporters (NPT) mRNAs in HeLa cells were determined by real-time PCR. PiT1 is most abundantly expressed in HeLa cells followed by that of PiT2; other NPTs are not detected. Error bars indicate S.E. B, transient inactivation of PiT1 in HeLa cells using siRNA. Proteins were extracted from HeLa cells transfected with 100 nm of the indicated siRNA, and PiT1 expression was analyzed by Western blot using anti-PiT1 antibody 48 h after transfection. C, depletion of PiT1 does not modify PiT2 expression, as measured by the relative mRNA expression levels (real-time PCR) of PiT1 (red bars) and PiT2 (blue bars) in shScramble or shPiT1 stably transfected HeLa clones. D, Pi transport was measured in transient and stable knockdown of PiT1 in HeLa cells. For transient knockdown of PiT1, HeLa cells were transfected with the indicated siRNA (10 nm) or untransfected (Untransf.), and Pi transport was determined 48 h after transfection. Stable shRNA clones were tested for Pi transport 4 days after seeding. **, $p<0.01$. E, transient depletion of PiT1 reduces cell proliferation. HeLa cells were transfected with 10 nm of two different PiT1-specific siRNAs (A and B), a pool of PiT2 siRNA, or untransfected. At 72 h after transfection, cells were counted. Cell numb, cell number. *, $p<0.05$. F, the proliferation of stably PiT1-depleted HeLa cells is impaired. Untransfected HeLa cells (crosses) or HeLa cells stably transfected with PiT1 shRNA (red circles) or scramble shRNA (white squares) were grown in complete medium and counted on the indicated days.

Figure 2:
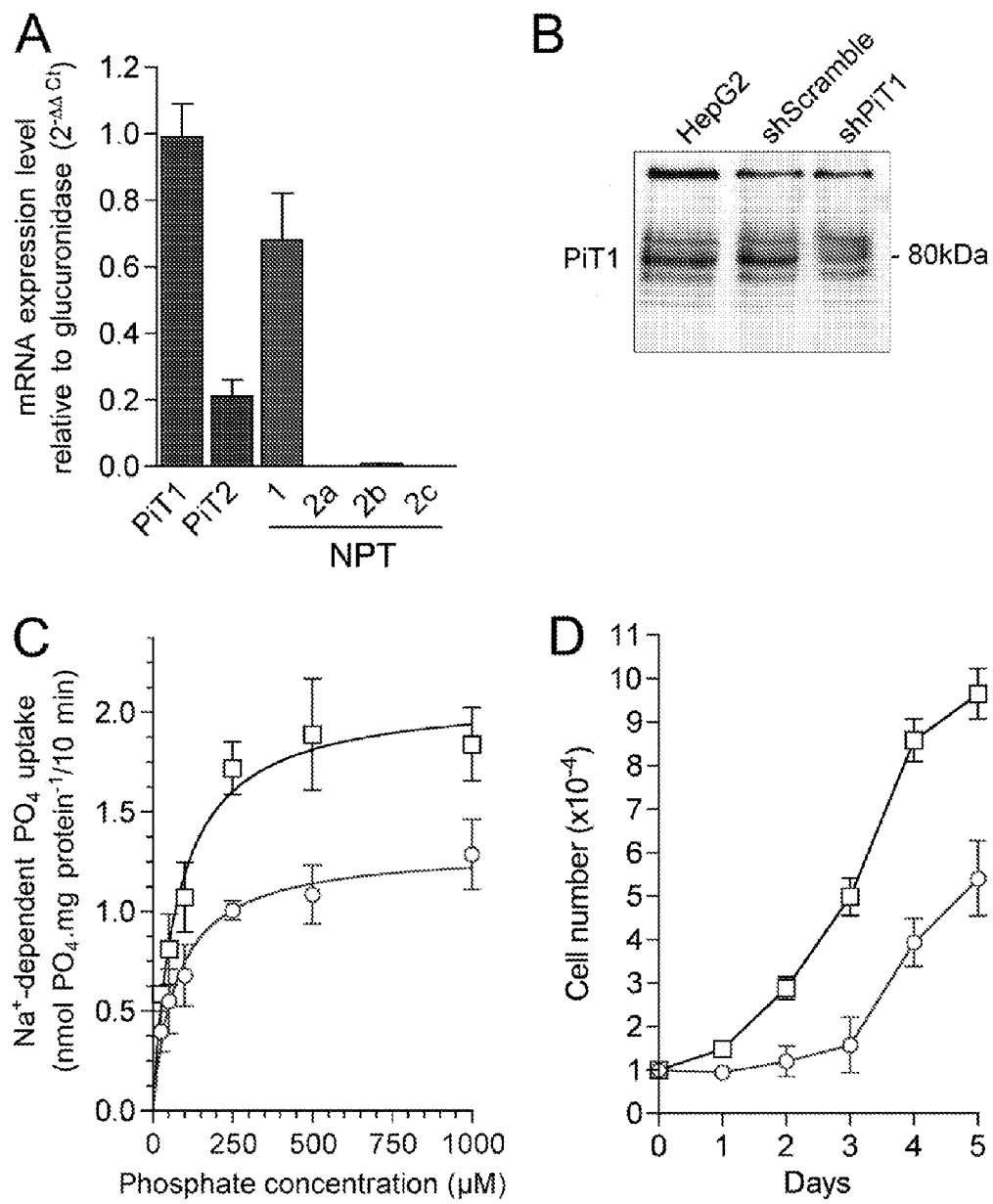

FIG. 2: Knockdown of PiT1 in HepG2 cells leads to reduced Pi transport and impaired proliferation. A, relative levels of NPT mRNAs in HepG2 cells using real-time RT-PCR reveals that PiT1 and NPT1 transporters are most abundantly expressed in HepG2 cells followed by that of PiT2; other NPTs are not significantly detected. Error bars indicate S.E. B, stable knockdown of PiT1 in HepG2 cells using shRNA. Proteins from HepG2 cells were extracted from untransfected cells (HepG2) or clones stably transfected with shScramble or shPiT1 in pSUPER vector, as indicated. PiT1 expression was analyzed by Western blot using anti-PiT1 antibody. C, $Na^+$-dependent Pi uptake in shScramble (square) and shPiT1 (circle) HepG2 cells were calculated by subtracting uptake measured under $Na^+$-free conditions from that observed in the presence of Na+ at each $KH_2PO_4$ concentration. D, HepG2 cells were grown in complete medium, stably transfected with shScramble (square), or shPiT1 (circle), and proliferation was assessed by counting the cells on the indicated days.

Figure 3:
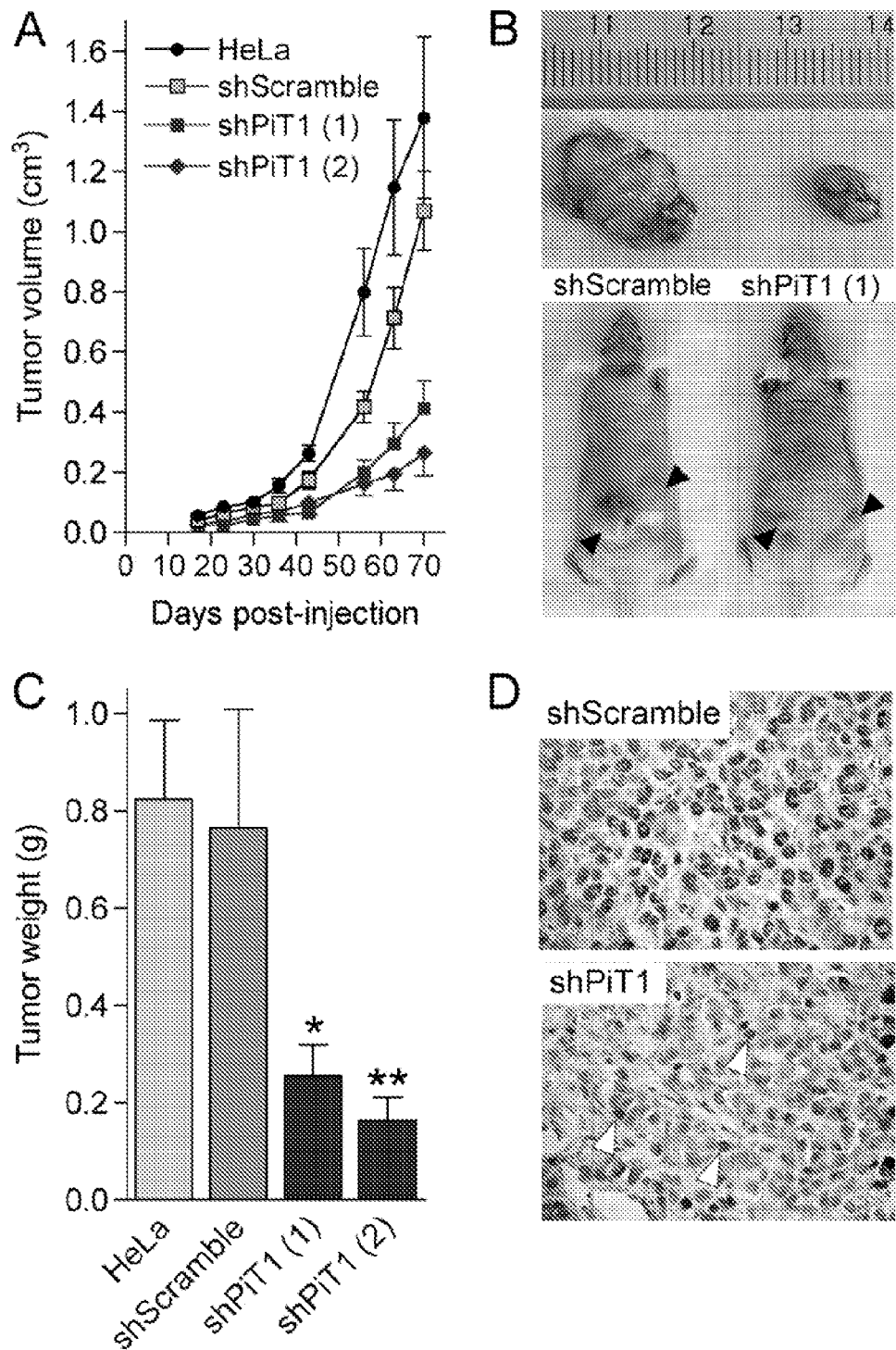

FIG. 3: PiT1 depletion in HeLa cells reduces tumor growth in nude mice. Subcutaneous injection of stably transfected shPiT1 HeLa cells in nude mice ($5 \times 10^6$ cells) resulted in tumor formation at a similar occurrence as shScramble HeLa cells, but the tumor growth rate (A), tumor size (B), tumor weight (C), and proportion of PCNA-positive cells in tumor sections (D) at sacrifice time (70 days after implantation) were severely reduced. *, $p<0.05$, **, $p<0.01$. Error bars indicate S.E.

Figure 4:
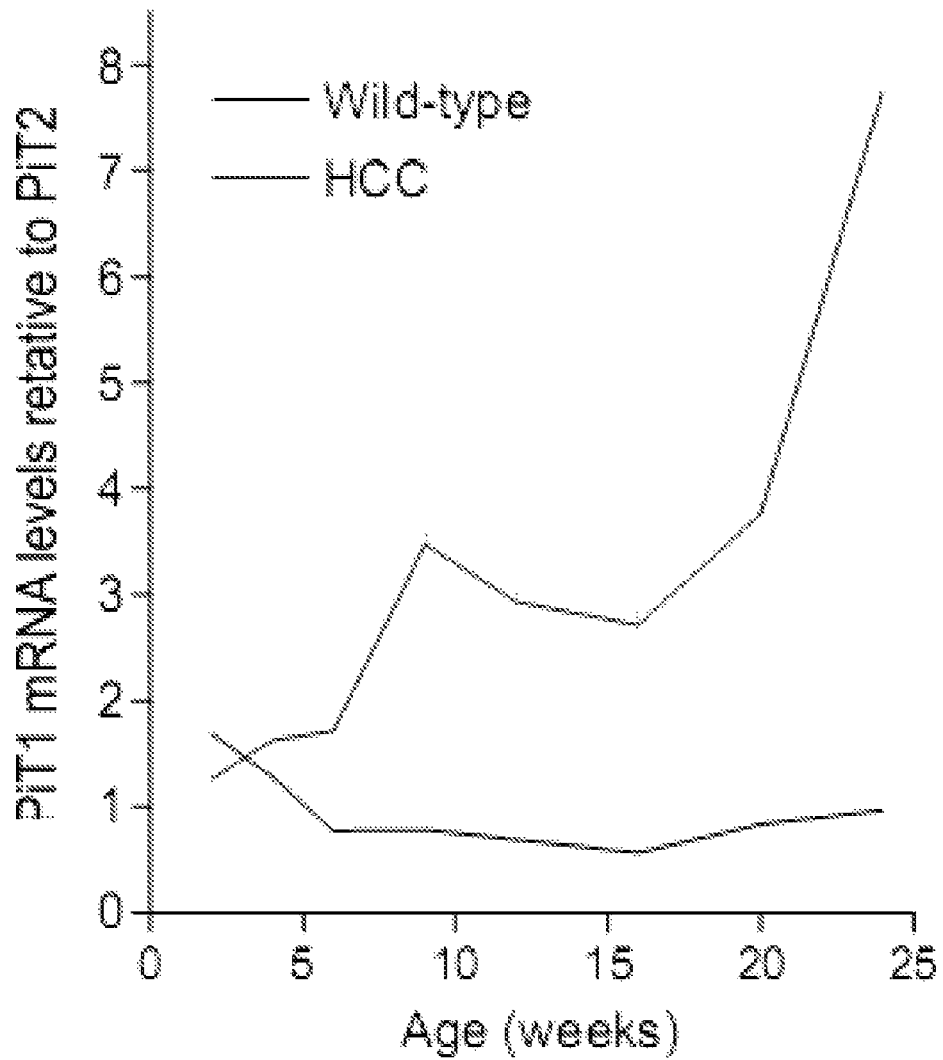

FIG. 4: Overexpression of PiT-1 in mouse hepatocellular carcinoma (HCC)

PiT1 and PiT2 expression were quantified using RT-qPCR in liver from 2 to 24-weeks old wild-type mice or mice overexpressing the large T antigen under the control of the antithrombin III promoter. Results are expressed as PiT1/PiT2 ratio, as indicated FIG. 5: Overexpression of PiT-1 in human hepatocellular carcinoma (HCC)

PiT1 and PiT2 expression were quantified using RT-qPCR in liver biopsies from healthy, cirrhotic and hepatocellular carcinoma patients, as indicated. Expression was related to the expression of β-glucuronidase expression.

Figure 6:
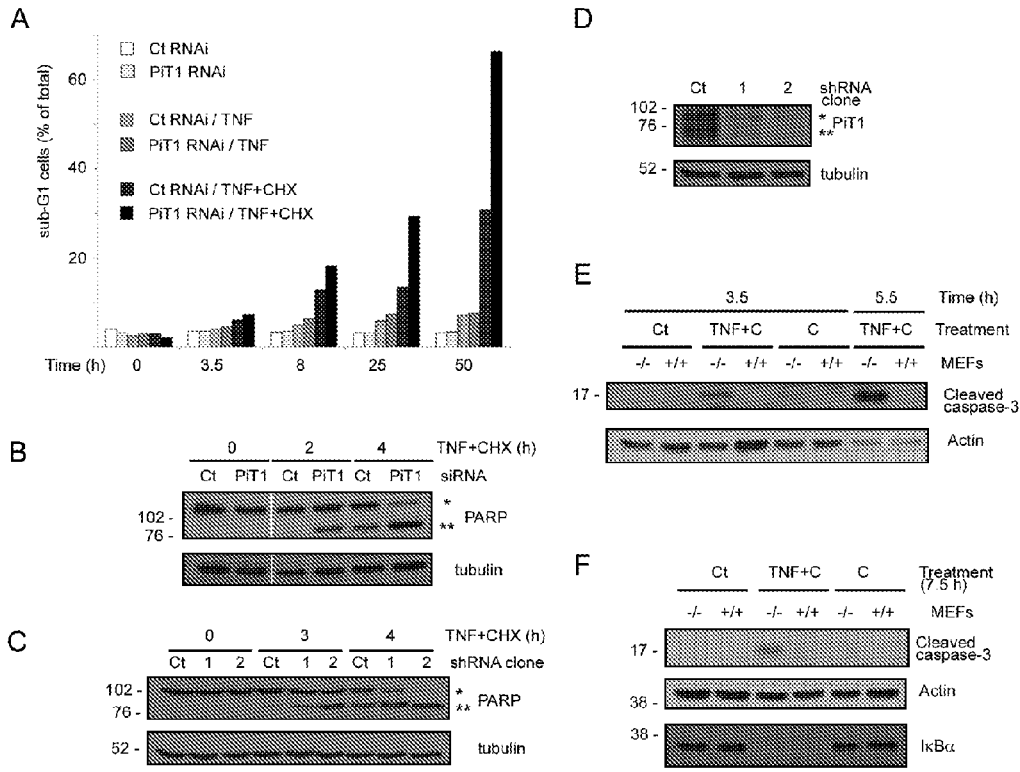

FIG. 6: PiT1 depleted cells are more sensitive to TNF induced apoptosis.

A and B, HeLa cells were transiently transfected with a siRNA control (Ct) or a siRNA directed against PiT1. 48 hours after transfection they were either left untreated or treated with 50 ng/ml TNF+/−10 µg/ml CHX for different times. A, Cells were stained with propidium iodide for the analysis of their DNA content and the % of cells with a subG1 staining was calculated. B, Cells were analyzed by western blot against PARP (*)/cleaved PARP () and tubulin as a loading control. C, HeLa cell clones stably expressing either a control (Ct) or a PiT1 shRNA (clone number 1 and 2) were treated with 50 ng/ml TNF and 10 µg/ml CHX for 0, 3 or 4 hours. Apoptosis induction was detected by western blot showing the cleavage of PARP (). The detection of tubulin was used as a loading control. D, Western blot showing the total amount of PiT1 protein expressed by the different clones. The PiT1 antibody is specific for the human protein and detects mainly two forms of the protein in HeLa cells indicated by * and **, which may differ by the glycosylation status. E and F, T SV40 immortalized MEFs from a knockout PiT1 embryo (−/−) or a WT littermate (+/+) were incubated with 50 ng/ml of human TNF and 10 (E) or 100 (F) µg/ml CHX (C) for different times. Cells were lysed and analyzed by western blot for the appearance of the cleaved form of caspase-3 and tubulin as a loading control (E and F) as well as the amount of IκBα (F).

EXAMPLE 1

Down-Regulating Expression of PiT1 Inhibits In Vitro and In Vivo Proliferation of HeLa Cells and HepG2

The results reported below were presented in a scientific article (Beck et al. 2009) which is incorporated herein by reference in its entirety.

Material & Methods

Culture Conditions, Transfections, and Growth Curves:

HeLa cells were maintained in Dulbecco's modified Eagle's medium supplemented with 5% FBS. The HepG2 cell line was cultured in a medium consisting of Dulbecco's modified Eagle's medium/Ham's F12, supplemented with 5 mg/liter insulin, $3.5 \times 10^{-7}$ M hydrocortisone hemisuccinate, 2 mM L-glutamine, and 10% FBS. HepG2 cells were seeded at $5 \times 10^3$ cells/cm², and medium was renewed every day. For siRNA and shRNA transfections, cells were seeded 24 h before the experiment in antibiotic-free medium at $3 \times 10^5$ or $5 \times 10^5$ cells/well in a 6-well plate, respectively. Cells were transfected with 10 nM siRNAs or 4 µg of plasmid using Lipofectamine 2000 in a serum-free medium. Four hours after transfection, 5% FBS was added to the medium. For growth curves, 25,000 cells were seeded in triplicate in 24-well plates. Cells were trypsinized and counted each day.

Production and Purification of an Anti-PiT1 Antibody:

A 59-amino acid peptide sequence from the central intracellular loop of PiT1 was fused to GST or to thioredoxine-V5-His6, expressed in BL21AI *E. coli* (Invitrogen), and purified from bacterial lysates on GSTrapFF columns (for GST-PiT1) or by using the HisTrap kit (for thioredoxine-PiT1-V5-His6 fusion protein) as per the manufacturer's instructions (GE Healthcare). Rabbits were immunized against human GST-PiT1 peptide (CovalAb), and the anti-PiT1 antibody was purified from rabbit serum by incubating the serum with pieces of polyvinylidene difluoride membrane blotted with 250 µg of purified thioredoxine-PiT1-V5-His6 protein. Elution was performed using 0.2 M glycine, pH 2, and the eluate was rapidly neutralized with 1 M Tris, pH 10. The purified anti-PiT1 antibody was diluted in Tris-glycine, pH 7.4, 50% glycerol, 0.1% bovine serum albumin.

RNA Interference:

Transient inactivation of PiT1 was assayed using siRNA SMARTpool® from Dharmacon (Chicago, Ill.) (catalog number L-007432-01) as per the manufacturer's instructions. Individual siRNA duplexes corresponding to the siRNA from the pool were then tested separately. Each individual siRNA gave comparable inactivation of PiT1 expression. Subsequent experiments were conducted with 10 nm PiT1 siRNA-A (5'P-UAUCAGUUCAGACCACUUGUU-3') and siRNA-B (5'P-UAUCUAUGCUGGUUUCCUCUU-3'). Transient reduction of PiT2 expression was achieved using siRNA SMARTpool® from Dharmacon (catalog number L-007433-01) used at 10 nm, as per the manufacturer's instructions. siCONTROL™ non-targeting siRNA 1 and siGLO™ RISC-free siRNA from Dharmacon were used as negative controls in transient transfection experiments. Stable knockdown of PiT1 expression was performed by cloning an shRNA corresponding to the sequence of siRNA-B into the pSUPER vector (Brummelkamp et al. 2002). The scramble sequence of shRNA-B was used as a negative control. HeLa cells were transfected with the pSUPER-shRNAs, plated at limiting density, and puromycin-resistant clones were picked, expanded, and tested for PiT1 expression. The data presented herein are from individual clones displaying at least an 80% knockdown of PiT1 expression. Experiments were performed with 3-4 independent stable transfectants, and the data presented illustrate representative clones.

Cloning of Human PIT1 and Site-Directed Mutagenesis:

Human PIT1 was PCR-amplified from human kidney cDNA. The PCR product was subcloned into pCR2.1 TA cloning vector (Invitrogen) and subsequently subcloned into the pcDNA6A expression plasmid (Invitrogen), in-frame with the V5 and His6 C-terminal tags. The integrity of the construct was verified by sequencing. Site-directed mutagenesis was used to introduce three silent mutations in the PiT1 sequence at the siRNA-B binding site to render the cDNA resistant to siPiT1-B cleavage (PiT1-RNAiR). The transport-deficient mutants of PiT1, S128A and S621A, were constructed by site-directed mutagenesis (QuikChange; Stratagene) from the PiT1-RNAiR construct.

Gene Expression and Quantification:

Total RNA was isolated from cells and tissue using NucleoSpin RNA columns (MACHEREY-NAGEL). Northern analysis of total RNA (25 µg) from HeLa cells was performed as described previously (11). For PCR detection of Na$^+$-Pi transporters, RNA (2 µg) was reverse-transcribed with 200 units of M-MLV-RT (Invitrogen) and PCR-amplified. PCR reactions contained 1× reaction buffer, 0.2 mm dNTPs, 1.5 mm MgCl$_2$, 0.25 µm each primer, and 0.05 units/µl Taq (Invitrogen). Cycle conditions were 94° C. for 1 min of initial denaturation followed by 36 cycles of denaturation (94° C., 15 s), annealing, and extension (72° C., 30 s). For gene quantification, RNA (2 µg) was reverse-transcribed with 200 units of M-MLV-RT (Invitrogen). Real-time PCR was performed using SYBR Green chemistry (Thermo Scientific) on an ABI Prism 7700 detection system. The glucuronidase gene was used as the reference gene, and expression differences were calculated as described previously (Livak et al., 2001).

Phosphate Uptake Measurements:

Transport of phosphate was measured as described previously (Escoubet et al., 1992). Apparent affinity constant ($K_m$) and maximal transport rate ($V_{max}$) were calculated by non-linear curve fitting, assuming Michaelis-Menten kinetics Xenographic Growth of HeLa Tumor in Athymic Mice and PCNA Immunodetection:

Outbred male athymic nude mice were obtained at 7 weeks of age from Elevage Janvier (Le Genest Saint Isle, France) and used for experiments at 8 weeks of age. Tumor formation was assayed by subcutaneously injecting 5×10$^6$ cells suspended in 100 µl of sterile PBS. Groups of five mice were injected at two sites per mouse. To measure the rate of tumor growth, the size of the tumor was monitored weekly using the formula: volume=(length×width$^2$)/2 (Tomayko et al. 1989). Mice and excised tumors were weighed 70 days after implantation (at time of sacrifice). Tumors were fixed in paraformaldehyde, and proliferating cell nuclear antigen (PCNA) immunodetection was performed using the M.O.M.™ immunodetection kit (Vector Laboratories) and anti-PCNA antibody (Dako), according to the manufacturer's instructions.

Statistics:

All graphs are plotted as mean±S.E. Statistics for dual comparisons were generated using Student's t tests, whereas statistics for multiple comparisons were generated using one-way analysis of variance followed by a suitable post hoc t test; *, p<0.05, **, p<0.01, for all statistics in the legends for FIGS. 1 and 3.

Results

The Na+-Pi Transporter PiT1 is Required for Proliferation of HeLa and HepG2 Cells:

Quantification of Na$^+$-Pi transporter expression in HeLa cells using real-time PCR revealed that PiT1 and PiT2 were the only Pi transporters expressed in these cells (FIG. 1A). Other described mammalian Pi transporters, namely NPT1, NPT2a, NPT2b, and NPT2c, were not detected. PiT1 expression was 2.1-fold higher than PiT2 in HeLa cells, in agreement with previous data obtained from cDNA microarrays hybridizations. The lack of expression of other Pi transporters in HeLa cells, together with the fact that inoculation of nude mice with HeLa cells is a classical model of tumorigenesis, make them an attractive system for the study of PiT protein function. As shown in FIG. 1B, knockdown of PiT1 expression in HeLa cells using two different siRNA constructs (siRNA-A and -B) was effective, as evidenced by Western blot analysis using a custom anti-PiT1 antibody. More detailed analysis of RNAi-mediated knockdown of PiT proteins was carried out. Northern analysis showed that PiT1 and PiT2 siRNAs induce a specific knockdown of the respective transporter expression, with no compensatory up-regulation of the remaining PiT. To study the prolonged effects of PiT1 inactivation, we generated an shPiT1 corresponding to the sequence of the siRNA-B and selected HeLa cell clones stably transfected with shPiT1-B plasmids. Real-time PCR data showed that in HeLa cells stably transfected by PiT1 shRNA, PiT1 mRNA expression was significantly decreased, whereas PiT2 expression was unchanged (FIG. 1C). A similar reduction in PiT1 protein levels was seen with shRNA as with transient siRNA experiments, and immunochemistry confirmed that plasma membrane labeling with anti-PiT1 antibody almost completely disappeared in HeLa cells stably transfected with PiT1 shRNA. As a result, both in transient and in stable RNAi experiments, Na$^+$-Pi transport function was reduced by 65-70% in HeLa cells (FIG. 1D). More detailed analysis of transport function reveals that the reduction in Pi transport was due to a reduced transport capacity ($V_{max}$shScramble=5.7±0.3 nmol·mg of protein$^{-1}$; $V_{max}$sh-PiT1=2.4±0.2 nmol·mg of protein$^{-1}$) rather than a change in transport affinity ($K_m$shScramble=150±16 µm; $K^m$sh-PiT1=132±11 µm). Because PiT1 and PiT2 have the same affinity for Pi, the reduction in Na$^+$-Pi uptake in HeLa cells is consistent with a decrease in PiT 1 protein abundance at the cell membrane.

We next evaluated the effect of PiT1 knockdown on the proliferation of HeLa cells. Transient transfection of two different PiT1 siRNAs led to a significant reduction in cell number, whereas unrelated siRNA (siControl) and PiT2 siRNA had no effect on cell proliferation (FIG. 1E). Stable expression of PiT1 shRNA showed that 4 or 5 days after equal seeding (i.e. at the time of exponential growth), the number of shPiT1 HeLa cells was half that of wild-type or shScramble HeLa cells (FIG. 1F). This result indicates that a wild-type level of PiT1 is necessary for normal proliferation of HeLa cells.

To exclude the possibility that the effect of PiT1-knockdown is specific to HeLa cells, PiT1 knockdown was performed in the non-tumorigenic HepG2 cell line, from hepatic origin. Expression analysis of the Na$^+$-Pi transporters showed that although PiT1 was the main transporter expressed in these cells, there was a high expression of NPT1 and a weaker expression of PiT2 (FIG. 2A). Stable inactivation of PiT1 using shRNA (FIG. 2B) resulted in reduced Na$^+$-Pi transport due to a decrease in the transport capacity ($V_{max}$sh-Scramble=2.08±0.16 nmol·mg of protein$^{-1}$; $V_{max}$sh-PiT1=1.31±0.12 nmol·mg of protein$^{-1}$) rather than a change in the transport affinity ($K_m$shScramble=75.1±10.9 µm; $K_m$shPiT1=75.3±15.3 µm) (FIG. 2C). Although the decrease in Na$^+$-Pi transport following shPiT1 knockdown was less prominent than in HeLa cells, the proliferation of HepG2 cells was similarly affected, and the cell number was half that of shScramble HepG2 clones 4 days after seeding (FIG. 2D).

PiT1 Depletion in HeLa Cells Reduces Tumor Growth in Nude Mice:

To evaluate whether PiT 1 depletion affects tumor growth in vivo, nude mice were injected subcutaneously with shScramble, shPiT1 stably transfected HeLa cells, or parental HeLa cells (FIG. 3A). At 7 days after inoculation, all animals developed a palpable tumor at the injection site. However, the rate of tumor growth in the shPiT1 groups (two independent clones) was significantly slower than the control groups when comparing either tumor volume (FIG. 3A) or tumor size (FIG. 3B). This difference became significant (p<0.05) by day 35. By day 70, the mean tumor size in shPiT1 mice was 0.41±0.09 and 0.26±0.07 cm$^3$, whereas in the control groups, it had reached 1.10±0.13 and 1.4±0.27 cm$^3$, corresponding to a 62-80% inhibition of tumor growth rate. Tumor weight was also decreased by 66-82% (FIG. 3C). Terminal deoxynucleotidyltransferase-mediated dUTP-biotin nick end-labeling staining of tumor sections revealed no difference in apoptotic cell number in the different tumors, whereas the number of PCNA-positive cells was much lower in shPiT1 HeLa cell-derived tumors (FIG. 3D). Taken together, these data indicate that reduced expression of PiT1 significantly inhibited tumor growth through decreased proliferation but did not affect tumor induction in nude mice.

EXAMPLE 2

Overexpression of PiT1 in Mouse and Human Hepatocellular Carcinoma (HCC)

Material & Methods
Gene Expression and Quantification:

Total RNA was isolated from liver biopsies (human or mice) using NucleoSpin RNA columns (MACHEREY-NA-GEL). RNA (2 µg) was reverse-transcribed with 200 units of M-MLV-RT (Invitrogen). Real-time PCR was performed using SYBR Green chemistry (Thermo Scientific) on an ABI Prism 7700 detection system. The glucuronidase gene was used as the reference gene, and expression differences were calculated as described previously. PiT1 to PiT2 ratios were also used to express the results obtained.

Results

Mice over-expressing the large T antigen under the control of the anti-thrombin III promoter were screened for PiT1 and PiT2 gene expression. The results show that over a 24-weeks period, PiT2 expression does not change (data not shown) whereas PiT1 expression (expressed as PiT1 to β-glucuronidase ratio, or as PiT1 to PiT2 ratios as shown in FIG. 4) increases drastically over time and became statistically significant as early as 9-weeks of age. Similar results were obtained for mice over-expressing the c-myc oncogène or in which the PTEN gene was specifically deleted in liver (Alb-Cre PTENlox/lox mice).

Figure 5:
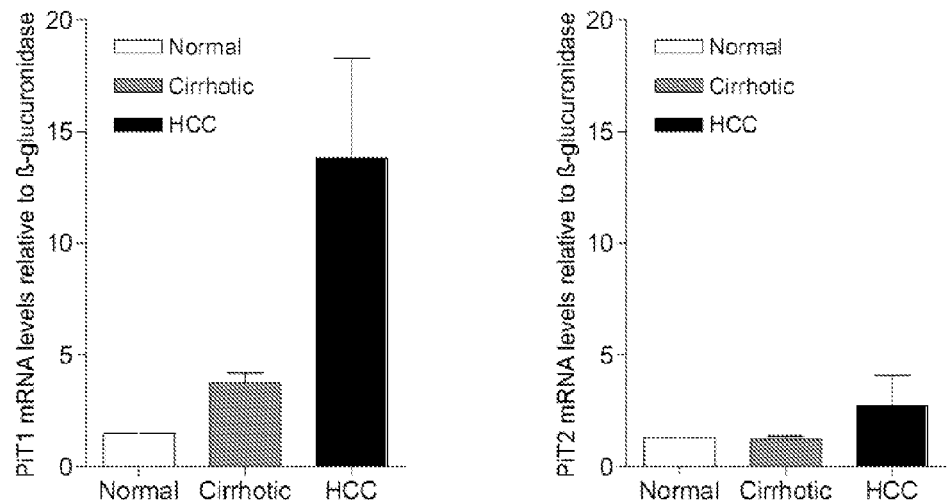

Liver biopsies were obtained from healthy patients or patients suffering from cirrhosis or hepatocellular carcinoma. Our data showed that although PiT2 expression was not different between the patients, PiT1 expression was increased 14-fold in HCC patients and 4-fold in cirrhotic patients (FIG. 5)

EXAMPLE 3

Down-Regulating Expression of PiT1 Sensitizes Both Human and Mouse Immortalized Cells to TNF-Alpha Material & Methods
Chemicals and Antibodies:

Human TNFα was purchased from Gentaur (Brussel, Belgium), L-JNKi and SP600125 from Merck-Calbiochem. DNase-free RNase, cycloheximide, propidium iodide, BI-78D3 and SP600125 were from Sigma. Lipofectamine LTX were obtained from Invitrogen. The following antibodies were purchased from Cell Signaling Technology: anti-phospho-SAPK/JNK (T183-Y185) (cat. number 9251), IκBα (cat. number 4814), RIP1 (cat. number 3493), cleaved caspase-3 (cat. number 9661), PARP (cat. number 9532), caspase-8 (cat. number 9746), AMPKα (cat. number 2532), phospho-AMPKα T172 (cat. number 2535). The human PiT1 antibody was produced in the laboratory and described in Beck et al. 2009. Monoclonal anti-β-actin clone AC-74 (cat. number A5316) or anti-β-tubulin clone TUB2.1 (cat. number T4026) were from Sigma. The monoclonal anti-V5 antibody (cat. number R960-25) was obtained from Invitrogen.

Cells:

HeLa cells and immortalized fibroblasts were grown in Dulbecco Minimum Essential medium (Gibco) supplemented with 5% Fetal Bovine Serum (Hyclone) and gentamicin (Gibco). Isolation of E12.5 MEFs was performed using established procedures (Nagy 2003). They were immortalized at passage 2 by the transfection (with Lipofectamine LTX) of a plasmid encoding the thermosensitive SV40 large T antigen under the human vimentin promoter and then grown at 33° C. HeLa cell clones stably expressing shRNAs were described in Beck et al. 2009.

Lentiviral Vector Stocks:

The introduction of the S621A mutation into PiT1 was previously described in Beck et al. 2009. The DNA constructs containing either WT PiT1 or PiT1 S621A were inserted in the lentiviral vector pHAGE-CMV-MCS-IZsGreenW. Two independent populations of cells were obtained for each construct by infecting cells with two distinct viral stocks. GFP-positive cells were enriched by fluorescent cell sorting.

Pi Uptake:

The transport of phosphate was measured as previously described in Beck et al. 2009.

Apoptosis Induction on Human and Mouse Cells:

HeLa cells were transfected with siRNAi as described in Beck et al. 2009. 48 to 72 hours before treatment. MEFs were split 48 hours before treatment. Apoptosis was induced by the treatment of cells with 50 ng/ml of human TNF and 10-100 µg/ml of cycloheximide in complete medium. When JNK inhibitors were used, the cells were pretreated for 30 minutes with the drug and then treated with TNF/CHX together with the drug.

Propidium Iodide Staining for DNA Analysis by Flow Cytometry:

Cells were transfected with the corresponding siRNAs 72 hours before treatment. All cells were collected (floating and attached), resuspended in PBS and fixed in cold 70% ethanol overnight (or longer) at 4° C. They were then washed in PBS and resuspended in a solution containing 0.02 mg/ml propidium iodide in PBS containing 0.1% Triton X-100, 0.2 mg/ml DNase-free RNase for 30 minutes at room temperature before FACS analysis. The DNA content was analyzed by flow cytometry on a BD Biosciences FACSCalibur flow cytometer with CELLQuest software.

Immunoblot Analysis:

Cells were placed on ice and floating cells were collected. Attached cell were rinsed once with NaCl 0.9% and this solution was used to wash the pellet of detached cells. Cells were then lysed by the addition of ice-cold lysis buffer (150 mM NaCl, 10 mM Tris-HCl, 5 mM EDTA, 1% NP-40, 0.5% deoxycholate, 0.1% SDS and complete protease inhibitor mix (Roche), 2 mM Na3VO4, 2 mM NaF, 5 mM NaPyrophosphate, 20 mM N-EthylMaleimide) on ice and detached with cell scrapers. The lysate was used to resuspend the pellet of detached cells and the combined lysate was left on ice for 30 minutes. Lysates were then centrifuged for 15 minutes at 16,000 g (4° C.) to remove insoluble materials and the supernatants were used for western blot analysis, which was performed as described in Beck et al. 2009. The numbers written on the left side of all western blot figures represent the molecular weight of proteins from the Full-Range Rainbow marker (cat. Number RPN800E) (Amersham), and each figure was chosen as representative of at least three independent experiments.

Statistics:

All graphs are plotted as mean+/−S.E. Statistics for dual comparison were generated using Student's t tests. *, $p<0.05$, , $p<0.005$, *, $p<0.0005$.

Results

The inventors showed that PiT1 depletion (but not PiT2) sensitizes both human and mouse immortalized cells to the pro-apoptotic activity of TNF. The re-expression of PiT1 in PiT1 knockout mouse fibroblasts delays TNF induced apoptosis. Importantly, the same protection is provided by the expression of a transport-incompetent mutant of PiT1, showing that the involvement of PiT1 in TNF induced apoptosis is independent of its Pi transport function. Finally, they showed that the sustained JNK activity is enhanced in PiT1 depleted cells and that JNK activity is instrumental in their death.

Acute or Stable PiT1 Depletion Sensitizes Immortalized Human and Mouse Cells to TNF Induced Apoptosis:

PiT1 was transiently depleted in the human carcinoma HeLa cell line with a siRNA (small interfering RNA) oligonucleotide. The efficiency of the siRNAs used in this study at downregulating the expression of the endogenous PiT1 protein in HeLa cells has been demonstrated previously (Beck et al. 2009). PiT1 depletion does not induce spontaneous apoptosis in this cell line, as detected by the lack of appearance of a population of cells having a sub-G1 DNA peak by FACS analysis (FIG. 6A). When treated with the pro-inflammatory cytokine TNF alone, HeLa cells (with or without PiT1) do not show any massive apoptosis. TNF is indeed a powerful inducer of the anti-apoptotic NFκB pathway, and the production of NFκB-dependent proteins needs to be inhibited for apoptosis to proceed (Karin 2006). We used the protein synthesis inhibitor cycloheximide (CHX) to sensitize cells to the pro-apoptotic activity of TNF. The addition of 10 µg/ml of CHX indeed triggers TNF induced apoptosis in HeLa cells. WT cells start showing some apoptotic staining by 8 hours, reaching 30% at 50 hours post treatment. PiT1 depleted cells were more sensitive to apoptosis, and the percentage of apoptotic cells was doubled at 25 and 50 hours post treatment compared to WT (wild type) cells. Apoptosis progression was also followed by the specific cleavage of PARP (poly ADP Ribose polymerase) a protein whose processing is under the control of the 'terminal caspase' caspase 3, which is an event that precedes DNA cleavage (FIG. 6B). PARP processing can be detected earlier (at 2 hours post treatment) and progresses faster (at 4 hours post treatment) in PiT1 depleted cells than in WT cells. We have also previously generated HeLa cell lines with a stable reduced expression of PiT1 by using a short hairpin RNA (shRNA) transfection (Beck et al. 2009). FIG. 6C shows that two different shRNA PiT1 clones are more sensitive to apoptosis than HeLa cells expressing a control shRNA, as shown by their increased PARP processing at 3 and 4 hours post TNF/CHX treatment. This shows that TNF mediated apoptosis is affected by either transient or stable PiT1 depletion. Moreover, this effect may be dependent on the amount of PiT1 still expressed by the cells, as clone 2, which expresses a lesser amount of PiT1 than clone 1 (FIG. 6D), is more sensitive to apoptosis than clone 1. Clone 2 was chosen for further experiments. In order to strengthen our results, we also tested whether we could reproduce them in a different cellular system. We immortalized mouse embryonic fibroblasts (MEFs) isolated from WT and PiT1 knockout E12.5 embryos (Beck et al. 2010) with SV40 large T antigen expression. As in HeLa cells, we treated these cells with TNF and 10 µg/ml of CHX. We chose to use the human TNF cytokine as it exclusively binds to mouse TNFR1 (and not TNFR2). FIG. 6E shows that PiT1 gene knockout increases the sensitivity to apoptosis of immortalized mouse fibroblasts, as detected by the early cleavage of caspase 3. The amount of CHX used so far (10 µg/ml) is actually not enough for a complete inhibition of NFκB dependent protein synthesis in response to TNF (Tang et al., 2001). As MEFs (as opposed to HeLa cells) can stand an increased amount of CHX without adverse short-term effects, we reproduced the last experiment with 100 µg/ml of CHX. This amount of CHX is indeed able to fully block the protein synthesis turned on by the activation of the NFκB pathway, as shown by the complete lack of IκBα de novo synthesis several hours after TNF stimulation (FIG. 6F). IκBα is indeed rapidly degraded in response to TNF stimulation and its re-synthesis normally starts within an hour, strictly under the control of the NFκB transcription factor (Tang et al., 2001). Once again, PiT1−/− cells are more sensitive to apoptosis than PiT1+/+ cells, as shown by the early activation of caspase-3, and CHX alone does not induce apoptosis. This amount of CHX was thereafter chosen for all subsequent experiments with mouse fibroblasts. Importantly, this may suggest that cells have an additional anti-apoptotic pathway (to the well-known NFκB pathway) that is impaired when PiT1 is absent. Alternatively, it is also possible that the absence of PiT1 activates a stronger pro-apoptotic signal in response to TNF.

Taken together, these data show that PiT1 absence (either by transient or stable RNA interference or gene knockout) increases the sensitivity to TNF mediated apoptosis in both human and mouse immortalized cells.

PiT1 Depleted Cells do not Show any Sign of Energetic Stress and PiT1 Involvement in TNF Mediated Apoptosis is not Linked to its Pi Uptake Function:

Because the well-described function of PiT1 is to provide cells with their Pi needs, and because Pi is a structural component of ribonucleotides, PiT1 depletion could therefore affect the cellular ATP availability. The AMPK (AMP activated protein kinase) is an extremely sensitive indicator of cell metabolic stress and get phosphorylated when the AMP:ATP ratio is increased (Towler et al., 2007). We therefore determined the basal phosphorylation status of AMPK in PiT1 depleted cells. We show that this kinase is neither phosphorylated in WT nor PiT1$^{-/-}$ MEFs, despite the presence of a functional enzyme, as demonstrated by its phosphorylation following the addition of the drug AICAR (5-amino-4-imidazolecarboxamide riboside), one of its specific activator (Towler et al., 2007). This observation therefore suggests that PiT1 depletion does not create any basal energetic stress.

HeLa cells also express PiT2/SLC20A2, the second Pi transporter encoded by the PiT/SLC20A family. PiT1 and PiT2 depletion reduce Pi uptake in HeLa cells. However, as opposed to PiT1 depletion, siRNA mediated PiT2 depletion (Beck et al. 2009) had no effect on the sensitivity of HeLa cells to TNF-induced apoptosis, showing that this effect is specific to PiT1 depletion. This specificity was further ensured by the use of two different siRNA oligonucleotides targeting distinct regions of the PiT1 mRNA in this experiment. Both are equally efficient at reducing the amount of endogenous Pit1 expressed by HeLa cells. Cells transfected with either PiT1 siRNA presented an enhanced cleavage of PARP than WT cells, strengthening the involvement of PiT1 in TNF-induced apoptosis. As opposed to cells expressing PiT1 siRNAs, cells transfected with a PiT2 siRNA did not show any increase in PARP cleavage and apoptosis, showing that this effect is specific to PiT1 depletion.

Finally, we wished to test more directly whether PiT1 involvement in TNF-mediated apoptosis was linked to its Pi uptake activity. We generated a transport incompetent mutant of PiT1 in which the serine at position 621 was replaced by an alanine Beck et al. 2009. The corresponding amino acid has been shown to be critical for Pi uptake within PiT2, but it does not affect the plasma membrane localization of the mutant proteins (Beck et al. 2009). We then inserted the V5-tagged construct (or the one encoding the WT PiT1 protein) into a lentiviral vector and stably transduced PiT1$^{-/-}$ MEFs with the recombinant viral stocks. For each construct, we characterized two independent populations (P1 and P2) of PiT1$^{-/-}$ MEFs expressing the recombinant proteins, detected with an anti V5 tag. As expected, PiT1$^{-/-}$ MEFs re-expressing a WT PiT1 protein display a significantly increased Pi uptake compared to the parental cells whereas Pi uptake was unaffected by the expression of the transport incompetent mutant PiT1 S621A. We show that the re-expression of WT PiT1 in PiT1$^{-/-}$ cells delays the appearance of the cleaved product of caspase-3, showing that PiT1 gene invalidation was indeed involved in the increased sensitivity of the cells to apoptosis. Importantly, the expression of the PiT1 S621A mutant protein also delayed apoptosis, as shown by the reduced cleavage of caspase-3. Both proteins were equally efficient at reducing the appearance of caspase-3 to 50% of the one displayed by the control PiT1$^{-/-}$ MEFs. These last experiments demonstrate that PiT1 involvement in TNF-induced apoptosis can therefore be uncoupled from its Pi uptake function.

Caspase-8 Activation is Increased by PiT1 Depletion in TNF-Induced Apoptosis:

We next wished to characterize the molecular mechanism underlying the increased sensitivity of PiT1 depleted cells to the pro-apoptotic activity of TNF. One of the first caspase to be activated during TNF-induced apoptosis is the initiator caspase caspase-8. We therefore investigated whether caspase-8 was more activated in PiT1 depleted cells. Western blot analysis could detect the cleavage of caspase-8 in its first processed form (p43/41) 3h30 after TNF treatment in HeLa cells expressing a control shRNA. However, caspase-8 processing was evident as early as 2 hours post TNF/CHX treatment in shRNA PiT1 HeLa cells, and the fully activated form (p18) could be detected by 3h30 in these cells. Consistent with this, we could also detect an important cleavage of RIP1 (receptor interacting protein 1), a caspase-8 substrate, at early time points in HeLa cells invalidated for PiT1. Similar results were obtained with mouse cells. RIP1 was cleaved earlier in PiT1$^{-/-}$ MEFs than in WT (wild-type) cells, showing that caspase-8 activation was, as in human cells, increased by PiT1 depletion in mouse cells. PiT1 depletion therefore impairs early events associated with TNF triggered apoptosis both in human and mouse immortalized cells.

Sustained JNK Activity is Increased in PiT1-Depleted Cells in Response to TNF/CHX:

It has become increasingly clear that the MAPK JNK is a major pro-apoptotic effector of TNF-induced apoptosis. TNFR1 stimulation induces a first very rapid and transient activation of JNK (30 minutes) in viable cells whereas in NFκB-inhibited cells, which are primed to undergo cell death, JNK is persistently activated and lasts for several hours. Sustained JNK activation (>1 hour) is indeed required for caspase 8 activation, and we therefore investigated whether JNK sustained activation could be modulated by PiT1 depletion. We show that JNK (all isoforms, indicated by * and ** on the figures) is more phosphorylated in PiT1 shRNA HeLa cells than in Ct shRNA cells in response to TNF/CHX at 2 or 3.5 hours post-treatment. This correlates well with an increase in apoptosis, detected by PARP cleavage. We reproduced the experiment by transiently knocking down PiT1 in HeLa cells. The transient depletion of PiT1 induces, consistently with our previous results, an increased sensitivity to TNF mediated apoptosis (as shown by PARP cleavage), which correlates with an increased phosphorylation of JNK. This shows that JNK over-activation is not due to an adaptation of the cell clones to the long-term depletion of PiT1. Moreover, siRNA mediated PiT2 depletion does not increase apoptosis and consistently, does not enhance the sustained JNK phosphorylation as compared to siRNA Ct treated cells, showing the specificity of the effect mediated by PiT1 invalidation. Finally, we show that these observations are also valid in mouse cells. Immortalized PiT1$^{-/-}$ MEFs present with an enhanced phosphorylation of JNK compared to PiT1$^{+/+}$ cells, which correlates well with the increased apoptosis detected by the appearance of cleaved caspase-3. Importantly, JNK enhanced activation therefore occurs in PiT1 depleted cells whether the NFκB is partly (HeLa cells) or fully inactivated (MEFs). The activation of NFκB pathway is the main pathway involved in the downregulation of the long lasting JNK activity in response to TNF. However, our results suggest that an additional pathway may be involved, at least in MEFs, when the NFκB pathway is totally impaired. This pathway would be invalidated in PiT1-depleted cells.

JNK Activity is Instrumental in TNF Induced Apoptosis in PiT1 Depleted Cells:

We next wished to test whether JNK activity could be responsible for the observed increased sensitivity to apoptosis in PiT1 depleted cells. We first treated HeLa cells with the JNK inhibitor SP600125, which acts as an ATP competitive inhibitor. We show that SP600125 reduces the appearance of cleaved PARP in HeLa cells transiently transfected with a PiT1 siRNA. SP600125 also reduces the phosphorylation of JNK detected in the cells. In order to rule out any off-target effect of the drug used, we next tested whether two other JNK inhibitors, JNKi and BI-78D3 could also prevent TNF-induced apoptosis on MEFs. These inhibitors act as substrate competitive inhibitors. JNK phosphorylation was reduced by the treatment with these inhibitors, and their use greatly delayed the cleavage of caspase-3. These results show that the hyper-activation of JNK is indeed involved in the increased sensitivity to apoptosis of PiT1-depleted cells.

Discussion:

The data presented here show that PiT1 depletion sensitizes cells to TNF/CHX mediated apoptosis. This can be reproduced either by acute or stable RNA interference in human cancer cells or by gene knockout in mouse immortalized fibroblasts. We show that this effect is specific to the invalidation of PiT1, as PiT2 depletion has no effect on this type of apoptosis. As PiT2 is also expressed in both HeLa cells and mouse fibroblasts, our results therefore show that PiT2 cannot compensate for the lack of PiT1. Because PiT1 functions as a Na-Pi symporter, PiT1 depletion reduces Pi uptake in cells, both in HeLa cells and immortalized MEFs. However, PiT1$^{-/-}$ mouse fibroblasts do not show any sign of major energetic stress, as shown by the absence of phosphorylation of the kinase AMPK, which rapidly reacts to fluctuations in the AMP:ATP ratio (Towler et al., 2007). Furthermore, PiT2 depletion, which also results in a decrease in Pi uptake, does not have any effect on apoptosis, suggesting that the increased sensitivity to TNF induced apoptosis revealed in PiT1 deficient cells is independent of its transport function. Finally, we show that the expression of a PiT1 mutant that cannot transport Pi is equally efficient at delaying apoptosis in PiT1$^{-/-}$ cells than is the wild type transporter. This undoubtedly demonstrates that PiT1 involvement in TNF induced apoptosis is uncoupled from its Pi transport activity. In accordance with this hypothesis, we have previously shown that PiT1 had another transport-independent function in the regulation of cancer cell proliferation (Beck et al. 2009).

We have initiated the dissection of the molecular mechanism underlying the increased sensitivity of PiT1 depleted cells to TNF induced apoptosis. The treatment of PiT1 depleted cells with TNF in pro-apoptotic conditions leads to the early activation of the initiator caspase caspase-8. The absence of PiT1 therefore impacts on early events induced by TNF. The activation of caspase-8 appears to occur through the formation of two distinct complexes in response to TNF (Wang et al., 2008). Complex IIA is formed via the association of TRADD (TNFR associated death domain), FADD (Fas associated death domain) and caspase-8 whereas complex IIB contains FADD, RIP1 and caspase-8. Our results suggest that complex IIB may constitute the main apoptotic complex that arises from TNF stimulation in our conditions. In agreement with this hypothesis, we show that RIP 1 is cleaved during the course of apoptosis in PiT1 depleted cells, suggesting that complex IIB indeed forms and thereby allows for the close association of caspase-8 with RIP1 that is necessary for RIP1 processing. Regardless of the type of pro-apoptotic complex that may form in PiT1 depleted cells, we have revealed an increased phosphorylation of JNK, which could be directly involved in caspase-8 activation. JNK has indeed been shown to be necessary for caspase-8 activation, probably within both complexes (Wang et al., 2008). Importantly, we show that JNK activity is instrumental in the apoptosis of PiT1 depleted cells, and three different JNK inhibitors indeed delay apoptosis in PiT1 invalidated human and mouse cells.

The regulation of JNK sustained activity in response to TNF is still incompletely understood. The production of anti-apoptotic proteins under NFκB control is the main protective mechanism that is turned on by TNF in most cells, and NFκB controls JNK activity duration. We show here that PiT1 depleted cells have an increased prolonged JNK activation, and that this is true whether the NFκB pathway is only partly (in HeLa cells) or fully inhibited (in MEFs) by increasing concentrations of CHX. This therefore suggests that PiT1 absence deregulates an anti-apoptotic pathway involved in the dampening of sustained JNK activity. This pathway would then be additional to the main NFκB pathway, as it protects WT MEFs when CHX fully inhibits NFκB-dependent protein synthesis. Alternatively, a stronger pro-apoptotic signal (resulting in an enhanced activation of JNK) may be triggered by TNF in cells depleted for PiT1. We are currently investigating the upstream kinases that are involved in JNK activation in PiT1 depleted cells and preliminary data show that both MKK4 and 7 (JNK direct upstream kinases) may be over-activated in response to pro-apoptotic TNF. It is also conceivable that PiT1 could bind to some intracellular proteins (via its large central hydrophilic domain (Beck et al. 2009)) involved in the composition of one of the multiple signaling complexes formed in response to TNF, and its absence would therefore affect the cell response.

Finally, considering that PiT1 (but not PiT2) mRNA seems to be transcribed in response to an activation of the NFκB pathway, it is possible that PiT1 expression could be increased during cancer cell progression, which may rely on an elevated NFκB activity (Karin 2006). Results presented here suggest that PiT1 may provide some protection to cancer cells against TNF induced apoptosis. Taken together with our recent results revealing the impaired proliferation of PiT1-depleted cancer cell (Beck et al. 2009), this may suggest that PiT1 could play a role during cancer pathogenesis.

EXAMPLE 4

PiT1/Proliferation Hepatocytes and MEFs

For this example, reference is made to the scientific article (Beck et al. 2010) which is incorporated herein by reference in its entirety.

This paper provides evidence showing that liver cells of mouse embryos KO for the gene coding for PiT1 undergo a decrease in proliferation and a massive wave of apoptosis, Conversely, overexpressing the PiT1 gene in a differentiated liver cell (hepatocyte) will trigger proliferation of the liver cell and thus constitute a means for obtaining large quantities of differentiated hepatocytes which may be used namely in toxicology assays or in cell therapy for replacing damaged liver tissue.

REFERENCES

Throughout this application, various references describe the state of the art to which this invention pertains. The disclosures of these references are hereby incorporated by reference into the present disclosure.

Beck L, Leroy C, Salaün C, Margall-Ducos G, Desdouets C, Friedlander G. (2009) J Biol Chem. 284(45):31363-74.

Beck L, Leroy C, Beck-Cormier S, Forand A, Salaün C, Paris N, Bernier A, Ureña-Torres P, Prié D, Ollero M, Coulombel L, Friedlander G. (2010) PLoS One. 10; 5(2):e9148.

Brummelkamp T. R., Bernards R., Agami R. (2002) Science 296, 550-553.

Escoubet B., Silve C., Balsan S., Amiel C. (1992) J. Endocrinol. 133, 301-309.

Karin, M. (2006) Nature 441, 431-436

Kurre P, Morris J, Miller A D, Kiem H P. (2001) Gene Ther. 8(8):593-9.

Livak K. J., Schmittgen T. D (2001) Methods 25, 402-408

Nagy, A. (2003) Preparing Mouse Embryo Fibroblasts (Manipulating the mouse embryo: a laboratory manual/Nagy, A., Gertsenstein, M., Vintersten, K., and Behringer, R. eds.), 3rd Ed., Cold Spring Harbor, N.Y.)

Tang, G., Yang, J., Minemoto, Y., and Lin, A. (2001) *Mol Cell* 8, 1005-1016

Tomayko M. M., Reynolds C. P. (1989) Cancer Chemother. Pharmacol. 24, 148-154.

Towler, M. C., and Hardie, D. G. (2007) *Circ Res* 100, 328-341

Wang, L., Du, F., and Wang, X. (2008) Cell 133, 693-703

---

The invention claimed is:

1. A method for treating a liver cancer in a patient diagnosed with liver cancer, comprising the step of administering an effective amount of an inhibitor of the activation of PiT1 to said patient in order to treat said liver cancer.

2. The method according to claim 1, wherein the inhibitor of the activation of the PiT1 is an agent down-regulating the expression of PiT1.

3. The method according to claim 1, wherein the agent down-regulating the expression of PiT1 is a small inhibitory RNA (siRNA).

4. The method according to claim 1, wherein the inhibitor of the activation of the PiT1 is an antibody against PiT1 or a fragment thereof.

5. The method according to claim 1, wherein an effective amount of a cytotoxic agent or a pro-apoptotic drug is also administered to said patient.

* * * * *

SEQUENCE LISTING

```
<160> NUMBER OF SEQ ID NOS: 3

<210> SEQ ID NO 1
<211> LENGTH: 357
<212> TYPE: PRT
<213> ORGANISM: Artificial
<220> FEATURE:
<223> OTHER INFORMATION: Synthetic polypeptide derived from Env Gibbon
      Ape Leukaemia Virus

<400> SEQUENCE: 1
```

Met Val Leu Leu Pro Gly Ser Met Leu Leu Thr Ser Asn Leu His His
1               5                   10                  15

Leu Arg His Gln Met Ser Pro Gly Ser Trp Lys Arg Leu Ile Ile Leu
            20                  25                  30

Leu Ser Cys Val Phe Gly Gly Gly Thr Ser Leu Gln Asn Lys Asn
        35                  40                  45

Pro His Gln Pro Met Thr Leu Thr Trp Gln Val Leu Ser Gln Thr Gly
    50                  55                  60

Asp Val Val Trp Asp Thr Lys Ala Val Gln Pro Pro Trp Thr Trp Trp
65                  70                  75                  80

Pro Thr Leu Lys Pro Asp Val Cys Ala Leu Ala Ala Ser Leu Glu Ser
                85                  90                  95

Trp Asp Ile Pro Gly Thr Asp Val Ser Ser Lys Arg Val Arg Pro
                100                 105                 110

Pro Asp Ser Asp Tyr Thr Ala Ala Tyr Lys Gln Ile Thr Trp Gly Ala
            115                 120                 125

Ile Gly Cys Ser Tyr Pro Arg Ala Arg Thr Arg Met Ala Ser Ser Thr
    130                 135                 140

Phe Tyr Val Cys Pro Arg Asp Gly Arg Thr Leu Ser Glu Ala Arg Arg
145                 150                 155                 160

Cys Gly Gly Leu Glu Ser Leu Tyr Cys Lys Glu Trp Asp Cys Glu Thr
                165                 170                 175

Thr Gly Thr Gly Tyr Trp Leu Ser Lys Ser Ser Lys Asp Leu Ile Thr
            180                 185                 190

Val Lys Trp Asp Gln Asn Ser Glu Trp Thr Gln Lys Phe Gln Gln Cys
        195                 200                 205

His Gln Thr Gly Trp Cys Asn Pro Leu Lys Ile Asp Phe Thr Asp Lys
    210                 215                 220

Gly Lys Leu Ser Lys Asp Trp Ile Thr Gly Lys Thr Trp Gly Leu Arg
225                 230                 235                 240

Phe Tyr Val Ser Gly His Pro Gly Val Gln Phe Thr Ile Arg Leu Lys

```
                      245                 250                 255
Ile Thr Asn Met Pro Ala Val Ala Val Gly Pro Asp Leu Val Leu Val
            260                 265                 270

Glu Gln Gly Pro Pro Arg Thr Ser Leu Ala Leu Pro Pro Pro Leu Pro
        275                 280                 285

Pro Arg Glu Ala Pro Pro Pro Ser Leu Pro Asp Ser Asn Ser Thr Ala
    290                 295                 300

Leu Ala Thr Ser Ala Gln Thr Pro Thr Val Arg Lys Thr Ile Val Thr
305                 310                 315                 320

Leu Asn Thr Pro Pro Pro Thr Thr Gly Asp Arg Leu Phe Asp Leu Val
                325                 330                 335

Gln Gly Ala Phe Leu Thr Leu Asn Ala Thr Asn Pro Gly Ala Thr Glu
            340                 345                 350

Ser Cys Trp Leu Cys
        355

<210> SEQ ID NO 2
<211> LENGTH: 21
<212> TYPE: RNA
<213> ORGANISM: Artificial
<220> FEATURE:
<223> OTHER INFORMATION: Synthetic PiT1 siRNA-A

<400> SEQUENCE: 2
uaucaguuca gaccacuugu u                                            21

<210> SEQ ID NO 3
<211> LENGTH: 21
<212> TYPE: RNA
<213> ORGANISM: Artificial
<220> FEATURE:
<223> OTHER INFORMATION: Synthetic PiT1 siRNA-B

<400> SEQUENCE: 3
uaucuaugcu gguuuccucu u                                            21
```